US007468796B2

(12) United States Patent
Luther et al.

(10) Patent No.: US 7,468,796 B2
(45) Date of Patent: Dec. 23, 2008

(54) MULTIPLE-COLOR MONOCHROMATIC LIGHT ABSORPTION AND QUANTIFICATION OF LIGHT ABSORPTION IN A STAINED SAMPLE

(75) Inventors: Edgar A. Luther, Wilmington, MA (US); Bruce Miller, Auburndale, MA (US)

(73) Assignee: CompuCyte Corporation, Westwood, MA (US)

( * ) Notice: Subject to any disclaimer, the term of this patent is extended or adjusted under 35 U.S.C. 154(b) by 83 days.

(21) Appl. No.: 11/200,524

(22) Filed: Aug. 8, 2005

(65) Prior Publication Data

US 2006/0033920 A1    Feb. 16, 2006

Related U.S. Application Data

(60) Provisional application No. 60/648,195, filed on Jan. 28, 2005, provisional application No. 60/599,521, filed on Aug. 6, 2004.

(51) Int. Cl.
    *G01J 3/51* (2006.01)
(52) U.S. Cl. .................. 356/411; 356/414; 356/419; 356/442; 356/72
(58) Field of Classification Search .......... 356/365, 356/370, 337–343, 320
    See application file for complete search history.

(56) References Cited

U.S. PATENT DOCUMENTS

| | | | | |
|---|---|---|---|---|
| 4,172,227 A * | 10/1979 | Tyrer et al. | ............... | 250/461.2 |
| 4,647,531 A | 3/1987 | Kamentsky | ............... | 435/7 |
| 5,072,382 A * | 12/1991 | Kamentsky | ............... | 382/133 |
| 5,107,422 A | 4/1992 | Kamentsky et al. | .... | 364/413.08 |
| 5,250,810 A * | 10/1993 | Geiger | ............... | 250/338.5 |
| 5,427,910 A * | 6/1995 | Kamentsky et al. | ............ | 435/6 |
| 5,523,207 A | 6/1996 | Kamentsky et al. | ............ | 435/6 |
| 5,587,833 A | 12/1996 | Kamentsky | ............... | 359/393 |
| 5,633,945 A | 5/1997 | Kamentsky | ............... | 382/129 |
| 5,885,840 A * | 3/1999 | Kamentsky et al. | ........... | 436/63 |
| 6,002,788 A | 12/1999 | Luther | ................ | 382/133 |
| 6,275,777 B1 * | 8/2001 | Shimizu | ............... | 702/30 |
| 6,312,914 B1 * | 11/2001 | Kardos et al. | ............... | 435/6 |
| 6,699,655 B2 * | 3/2004 | Nikiforov | ............... | 435/4 |
| 6,819,787 B2 | 11/2004 | Stone et al. | ............... | 382/133 |
| 6,822,742 B1 * | 11/2004 | Kalayeh et al. | ............ | 356/437 |

(Continued)

FOREIGN PATENT DOCUMENTS

DE    196 02 145 A1    7/1997

(Continued)

OTHER PUBLICATIONS

Luckey, J.A., Drossman, H., Kostichka, A.J., Mead, D.A., D'Cunha, J., Norris, T.B., and Smith, L.M, "High Speed DNA sequencing by capillary electrophoresis", 1990, Nucleaic Acids Research, vol. 18, No. 15.*

(Continued)

*Primary Examiner*—F. L Evans
(74) *Attorney, Agent, or Firm*—Bromberg & Sunstein LLP

(57) ABSTRACT

An absorption detection system is provided. The system includes a plurality of monochromatic light sources and a separator for separating the light from the plurality of monochromatic light sources into a plurality of wavelengths. A plurality of detectors, receives light of a single wavelength to measure absorption of light in a biological sample.

32 Claims, 23 Drawing Sheets

U.S. PATENT DOCUMENTS

| | | |
|---|---|---|
| 6,859,276 B2 * | 2/2005 | Xu ............................. 356/336 |
| 7,106,442 B2 * | 9/2006 | Silcott et al. ................ 356/338 |
| 2002/0176069 A1 * | 11/2002 | Hansen et al. ................ 356/73 |
| 2003/0058440 A1 * | 3/2003 | Scott et al. .................. 356/318 |
| 2004/0071332 A1 | 4/2004 | Bruce et al. ................. 382/133 |
| 2005/0190365 A1 | 9/2005 | Luther ....................... 356/338 |

FOREIGN PATENT DOCUMENTS

| | | |
|---|---|---|
| WO | WO99/45094 A1 | 9/1999 |
| WO | WO03/016875 A2 | 2/2003 |
| WO | WO03/093795 A2 | 11/2003 |

OTHER PUBLICATIONS

Steinkamp, J.A., and Stewart, C.C., "Dual-Laser, Differential Fluorescence Correction Method for Reducing Cellular Background Autofluorescence", 1986, cytometry, vol. 7, p. 566-574.*

International Search Report dated May 2, 2006.

Zbigniew Darzynkiewicz et al., Laser-Scanning Cytometry: A New Instrumentation with Many Applications; Experimental Cell Research 249, 1-12 (1999); Article ID excr. 1999.4477.

International Search Report dated Jan. 17, 2006, received on Jan. 23, 2006.

* cited by examiner

Blue laser analysis

Red laser analysis

Mosaic Color Absorption Image

Light Loss and Shaded Relief Images

Shaded Relief

Light Loss

Application of Compensation

Uncompensated

Blue

Green

Red

Compensated for DAB overlap

Green Comp.

Red Comp.

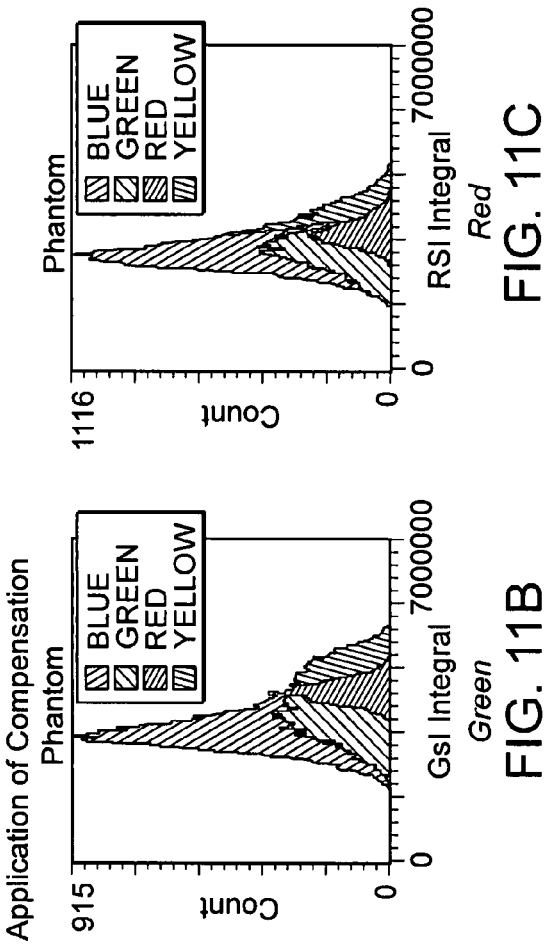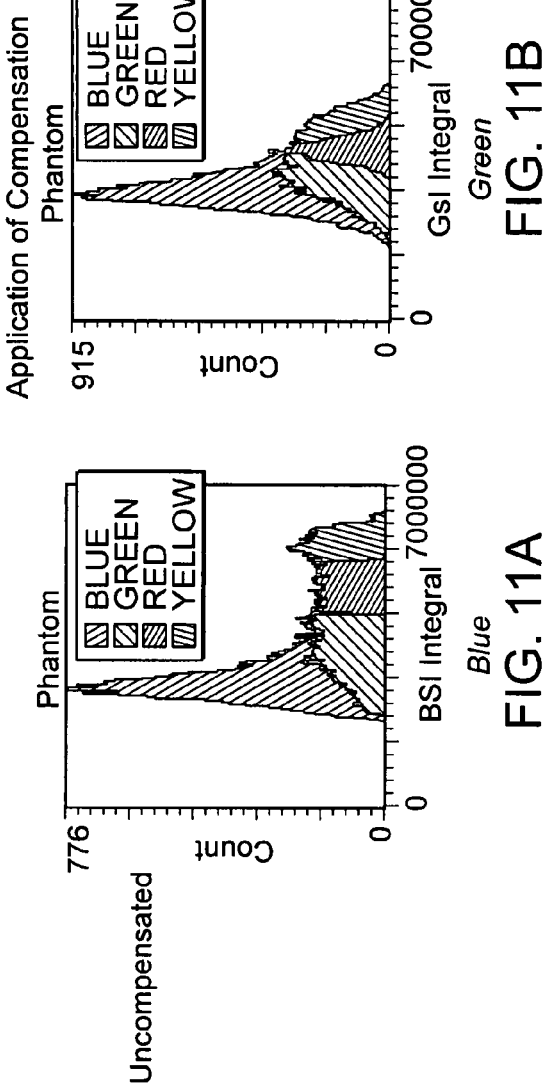
FIG. 11A FIG. 11B FIG. 11C FIG. 11D FIG. 11E

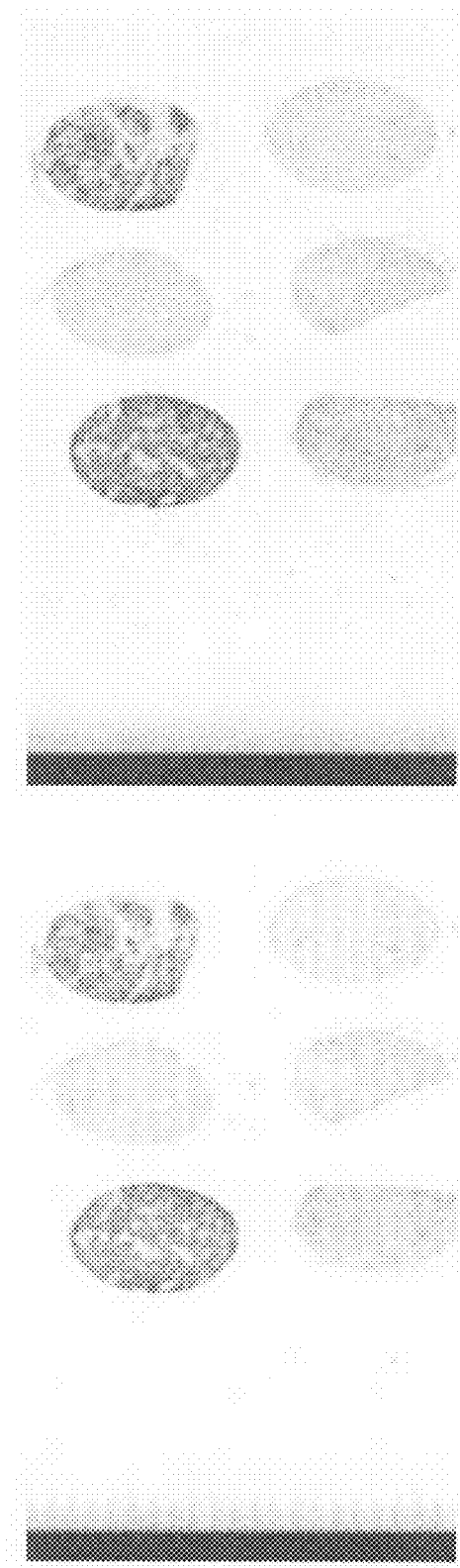

MULTIPLE-COLOR MONOCHROMATIC LIGHT ABSORPTION AND QUANTIFICATION OF LIGHT ABSORPTION IN A STAINED SAMPLE

The present application claims priority from U.S. Provisional Application No. 60/599,521, filed Aug. 6, 2004, and U.S. Provisional Application No. 60/648,195, filed Jan. 28, 2005. Each of these applications is hereby incorporated herein, in its entirety, by reference.

TECHNICAL FIELD

The present invention relates to laser scanning cytometry and, more particularly, to imaging systems and methods employing multiple-color laser absorption for analysis of tissue or cellular samples stained with chromatic, fluorescent or other dyes.

BACKGROUND ART

Laser scanning cytometry ("LSC") is a technology where one or more laser beams are scanned across an analysis surface which typically contains cells or tissue. Photomultiplier tubes and photodiodes are used to detect fluorescent light emitted from the samples as well as modifications to the interrogating laser light. The outputs of the detectors are digitized, and synchronous movements of a computer controlled microscope stage allow accumulation of computer memory arrays of detector outputs that can be treated as images of the areas of the specimen scanned. The memory arrays differ from camera-based images in that there is not a one-to-one correspondence between the pixel areas of the image and the physical area of the slide; instead, a variable-sized evaluation area is centered about the pixel location. The array "images" are segmented by a number of methods to identify events of interest. Quantitative data is calculated for each event and multi-feature data is analyzed for each of many thousands of events in a typical analysis.

U.S. Pat. Nos. 5,072,382 and 5,107,422 describe the general operation of laser scanning cytometers. U.S. Pat. No. 6,002,788 describes details of laser light scatter, light loss and absorbance measurements. Each of the above patents are hereby incorporated here by reference.

Light scatter and absorption may also be measured by a LSC system using a photodiode detector. In accordance with one such system, a blocker bar is placed between a laser beam and a detector. When a cell or other object interferes with the laser beam, light scattered by the object bypasses the blocker bar and strikes the detector, producing an increased signal. The resultant image has a dark background with bright areas where cells or other objects are present. This type of light scatter is analogous to the light scatter used in flow cytometry and is often used for the initial identification of cells.

A variation of light scatter measurement may be used to obtain bright field images of cells with a high degree of morphological detail. This is accomplished by varying the position of the blocker bar to allow a portion of the laser beam to impinge on the detector at all times. The signal produced by the portion of the laser which impinges on the detector at all times serves as a reference signal. As cells and other objects interact with the laser beam, structures within them scatter and/or absorb light and modulate the strength of the reference signal. (An example of such an LSC and system is described in U.S. Pat. No. 6,002,788.)

Another variation of laser light measurement is the "light loss mode." In accordance with this variation, no blocker bar is employed. The laser beam continuously impinges on the detector and produces a high reference signal. When objects interact with the beam signal strength is diminished. Refractile objects, such as beads and spherical cells, will refract light away from the detector and chromatically stained objects, such as cells in a tissue section, will absorb the laser light. In both cases bright-field images are produced with dark objects. These images are often digitally inverted so that they can be analyzed in a manner similar to fluorescence-based analysis. (An example of such an LSC and system is described in co-pending U.S. patent application Ser. No. 11/040,183, entitled "Method and Device for Interrogating Samples Using Laser Scanning Cytometry and Other Techniques" and filed Jan. 21, 2005, which is hereby incorporated herein by reference.)

Most laser scanning cytometers are equipped with multiple lasers to excite a wide variety of fluorescent dyes. Often this analysis is done in a multiplexed fashion, where a scan area is first scanned with one color laser and then the same scan area is scanned with a second color laser. The data from both scans are combined and images are interchangeable. (An example of a LSC system employing multiple lasers is described in U.S. Pat. No. 5,885,840, which is hereby incorporated herein by reference.)

In accordance with multiple laser LSC systems, for each scan pass, laser scatter or absorption can be obtained. Chromatic dyes absorb light at different portions of the electromagnetic spectrum, with the combination of the interrogating wavelengths and the dyes' absorption spectral response giving the dyes their distinctive colors. For each laser used, there will be differential absorption of the beam by the different dyes used to the stain the sample. In a standard iCyte® LSC system (manufactured by Compucyte Corporation of Cambridge, Mass.), blue laser absorption can be obtained along with red laser absorption, as seen in FIGS. 1A and 1B.

As noted above, multi-color fluorescence technology has developed, largely in the area of flow cytometric analysis. Research-grade instruments are capable of measuring up to 12 colors of fluorescence on individual cells using a combination of multiple excitation lasers and a plurality of photomultiplier tubes coupled to discrete bandwidth filters. One problem encountered in performing multi-color fluorescence analysis is spectral overlap, where the fluorescence emission spectrum of a dye extends into the bandwidths measured by several detectors. Compensation techniques have been developed that can correct for this spectral overlap by taking a proportion of the signal from an interfering dye's detector and subtracting it from the signal being quantified.

In the biological arts, tissue analysis is often performed using sections of tissues that have been stained with chromatic dyes. Such techniques are often applied in connection with research pathology, drug discovery and validation, biomarker discovery, and drug safety procedures based on tissue analysis. Chromatic dyes are traditionally examined by techniques related to bright field microscopy, and methods of evaluating chromatically stained samples include (1) manual scoring (0, to +++), depending on various factors including the staining intensity and the number of cells stained and (2) automated image analysis techniques using images obtained by digital photo-microscopy of samples where the optical density measurements are used as the metric.

One of the inherent problems in undertaking quantitative analysis of tissue sections is the fact that tissues are heterogeneous in nature, and they often contain varying levels of either endogenous or preparation-associated auto-fluorescence. This auto-fluorescence is known to interfere with fluorescence analysis. Correction for auto-fluorescence is a distinct process, different from spectral overlap correction. Methods to correct for the interference of auto-fluorescence associated with fluorescence using multiple wavelength laser excitation are known in the art. (See, for example, Lee, M., Luther, E. (2004). "*Using virtual channels to perform compensation and correct background autofluorescence in laser scanning cytometry.*" ISAC XXII International Congress. *Cytometry Part A* 59A(1): 27-73.

Methods have also been described to convert color camera RGB or HSL values to dye equivalents. See, for example, U.S. Pat. No. 6,819,787 issued to Stone et al. and Ruifrok et. al., *Comparison of Quantification of Histochemical Staining by Hue-Saturation-Intensity (HIS) Transformation and Color-Deconvolution. Applied Immunohistochemistry and Molecular Morphology*, vol. 11(1), pp. 85-91, March 2003. However, these methods have the disadvantage that broad spectrum light is used as the light source, resulting in less control of the spectral characteristics of the fluorochromes being evaluated.

SUMMARY OF THE INVENTION

In accordance with one embodiment of the invention, an absorption detection system includes a plurality of monochromatic light sources and a separator for separating the light from the plurality of monochromatic light sources into a plurality of wavelengths. Each of a plurality of detectors receives light of a single wavelength to measure absorption of light in a biological sample. The monochromatic light sources may produce light directed at the biological sample containing a dye such that light passes through the sample, and the separator may separate light that has passed through the sample.

In accordance with related embodiments, at least one of the monochromatic light sources may be a laser. Further, a beam of light from each of the plurality of monochromatic light sources may be received by the sample such that the beams are coaxial. The separator may include a beam-splitting mirror for receiving light from the monochromatic light sources. Similarly, the separator may include a band-pass filter for receiving light from the beam-splitting mirror. Further, the separator may include a prism. In accordance with other related embodiments, at least one detector may include a photodiode and/or at least one detector may include a photomultiplier tube.

In accordance with yet another related embodiment, a beam of light from at least one monochromatic light source may be divided into two portions by the beam-splitting mirror. The two portions may be received by two separate detectors and/or the two separate detectors may have different signal acquisition characteristics. The acquisition characteristics may include absorption and low-angle light scatter.

In accordance with a further related embodiment, a signal from at least one detector is filtered to match a wavelength of light produced by at least one of the plurality of monochromatic light sources. In accordance with yet another related embodiment, the system may include two polarizing filters that may be oriented perpendicular to one another and each of the polarizing filters may receive one of the two portions. The two detectors may measure orthogonal polarization states. In accordance with another related embodiment, the wavelengths of the monochromatic light sources may correspond to the wavelengths absorbed by the dye.

In accordance with another embodiment of the invention, a method for detecting light absorption includes directing a plurality of monochromatic beams of light to a surface containing a biological sample and separating the light received at the surface into a plurality of wavelengths of light. Light of a single wavelength is detected at each of a plurality of detectors to measure absorption of light in the sample.

In accordance with related embodiments, directing a plurality of monochromatic beams of light to the surface may include directing at least one laser beam to the surface and/or directing a plurality of monochromatic beams of light to the surface may include directing the beams to the surface such that the beams are coaxial when received by the surface. Separating the light received at the surface may include receiving the light at a mirror.

In accordance with another related embodiment, the method further includes receiving light from the mirror at a plurality of band-pass filters. In accordance with other related embodiments, separating the light received at the surface may include receiving the light at a prism and/or detecting light of a single wavelength may include detecting light of a single wavelength at each of a plurality of photodiodes and/or photomultiplier tubes.

In accordance with further related embodiments, at least one monochromatic beam of light may be separated into two portions and/or the two portions may be received by two separate detectors. The two separate detectors may have different signal acquisition characteristics. The different signal acquisition characteristics may include absorption and low-angle light scatter. Further, the two portions may be received by two polarizing filters, the polarizing filters may be oriented perpendicular to each other and the two detectors may measure orthogonal polarization states.

In accordance with yet another related embodiment, directing a plurality of monochromatic beams of light to the surface may include directing N monochromatic beams of light to the surface and detecting light of a single wavelength at each of a plurality of detectors to measure absorption of light in the sample may include detecting light of a single wavelength at each of the plurality of detectors to measure the absorption of N dyes in the sample. Each of the N dyes may absorb a percentage of light from each of the N monochromatic beams of light and a one-to-one correspondence between each dye and any given monochromatic beam of light may be established. Establishing a one-to-one correspondence may include algebraically compensating for an overlap in absorption due to any of the N dyes absorbing light at more than one wavelength and algebraically compensating for the overlap may include solving a system of N simultaneous equations.

In accordance with another related embodiment, at least one of the N dyes may comprise an off-color dye and algebraically compensating for an overlap in absorption due to any of the N dyes absorbing light at one wavelength may include measuring absorption at a first wavelength, measuring absorption at a second wavelength, multiplying the measurement taken at the second wavelength by a ratio of the measurement taken at the first wavelength to the measurement taken at the second wavelength to produce a compensation factor and subtracting the compensation factor from the measurement taken at the first wavelength. Detecting light of a single wavelength at each of a plurality of detectors may include detecting light of a single wavelength at up to N detectors and detecting light of a single wavelength at up to N detectors may include simultaneously detecting light of a single wavelength at up to N detectors.

In accordance with a further related embodiment, detecting light of a single wavelength to measure absorption of dye in the sample may include detecting fluorescence and/or autofluorescence emitted by the sample and the method may further include using a signal produced by the fluorescence and/or auto-fluorescence to quantify the absorption of dye in the sample.

In accordance with yet a further related embodiment, signals produced in accordance with variations of intensity when the beams impinge upon a blank surface may be measured and a per-pixel correction lookup table may be created. Values associated with the signals produced when the beams impinge upon the blank surface may be used to compensate for intensity variations produced when the beams impinge upon the sample Detecting signals produced in accordance with the variations of intensity may include creating a per-pixel correction lookup table containing values associated with the detected signals. Detecting signals produced in accordance with variations in the intensity of the beams of monochromatic light may also include detecting systemic, optically induced variations in the intensity.

In accordance with another embodiment of the invention, a method for quantifying the light absorption in a biological sample (such as a chromatically stained sample) includes impinging a beam of light on the sample and measuring an amount of light loss due to interference of the beam by the sample to produce a first signal. An amount of fluorescence emitted by the sample is measured and a second signal is produced. The second signal is used to correct the first signal in order to quantify the amount of light loss due to a dye in the sample. In accordance with a related embodiment, measuring the amount of fluorescence emitted by the sample may include measuring the amount of auto-fluorescence emitted by the sample and/or measuring the amount of fluorescence emitted by the sample may include measuring the amount of green fluorescence emitted by the sample. Impinging a beam of light on the sample may include impinging at least one laser beam of light on the sample.

In accordance with a further embodiment of the invention, an apparatus for quantifying light absorbance in a biological sample includes a light source for producing a beam of light to be impinged on the sample. A detector detects an amount of light loss due to interference to the beam by the sample and produces a first signal. A photomultiplier detects the amount of fluorescence emitted by the sample and produces a second signal. Data associated with the first and second signals is received at a processor and the data associated with the second signal is used to quantify the amount of light loss due to dye in the sample.

BRIEF DESCRIPTION OF THE DRAWINGS

The foregoing features of the invention will be more readily understood by reference to the following detailed description, taken with reference to the accompanying drawings, in which:

FIGS. 11A-11E are illustrations of histograms of the random sampling elements of uncompensated data for the three detectors employed and compensated data for the overlap of DAB chromogen into the green and red channels;

FIGS. 22A and 22B are illustrations of light absorption images produced before and after per-pixel correction is applied, respectively.

DETAILED DESCRIPTION OF SPECIFIC EMBODIMENTS

Figure 1A:
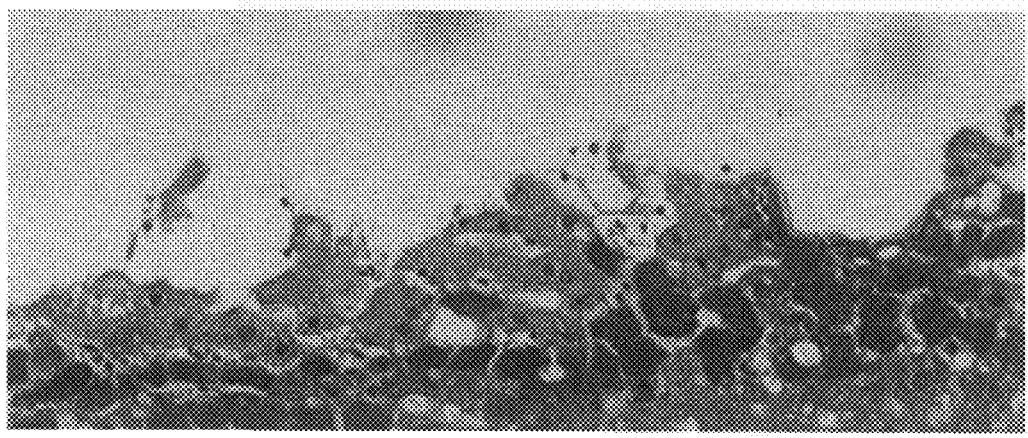
FIGS. 1A and 1B are illustrations showing images produced in accordance with a prior art LSC system, where the laser absorbance was measured in sequential scans with different excitation wavelengths.
Figure 1B:
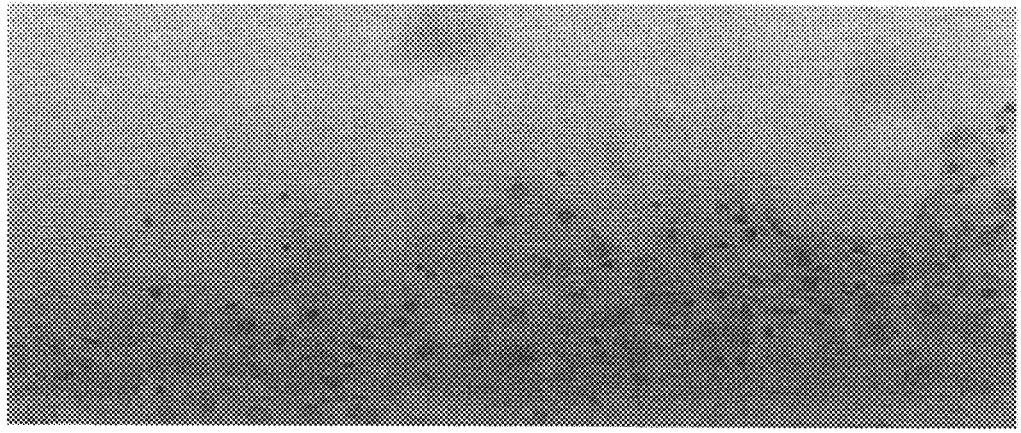

Light absorption is the process by which colors are generated, and RGB (red, green, blue) describes the possible colors available in a given system. Red, green and blue are the primary colors and from combinations of these colors, any other color can be generated. A system for three-color absorption gives the advantage of being able to cover more of the color map; for that reason, a three-color absorption system has been designed in accordance with embodiments of the present invention.

As discussed above, laser scanning technology is a quantitative technology that can reliably calculate the amount of staining of markers for fluorescent dyes. The same principles hold true for absorption measurements. After events are segmented (or by using other sampling methods), the amount of staining for each of the constituents may be quantified. A method is described herein for correcting the resultant detector measurement arrays (images) for variation in the laser illumination.

Measurements of absorbance and fluorescence, along with combinations of the two, are useful analytical tools, with overlap in the areas where they might be used. In general, fluorescent dyes are thought to be capable of producing better quantitative data than chromatic dyes, but chromatic dyes are more easily visualized. Chromatic dyes are more commonly used than fluorescent dyes, in part for historical reasons, but also because they require less expensive equipment for readouts, are more permanent, and are more widely accepted. Much archival material is in the form of chromatically dyed sections and samples; there is a need to quantify the staining in chromatically dyed sections and samples.

For example, in the area of toxicologic pathology, large-scale studies are often done, and the results have very significant implications in the very expensive process of drug discovery. If something goes wrong in an experimental study, the results need to be investigated and reanalyzed. Often the material from the original studies is in the form of chromatic stained slides and thus absorbance analysis capabilities are necessary. Thus, there are applications where automated tissue analysis would be useful for pathological diagnosis.

In accordance with an embodiment of the present invention, a series of slides may be scanned automatically to detect events of importance that may be missed during a cursory examination by a pathologist. In this scenario, the slides are scanned first by the instrument, and then events of interest are automatically determined, based on the quantitative data. In the second stage of the analysis, the pathologist makes the actual determination. Here the instrument would bring pre-identified cells or objects of interest to the proper location on the viewing microscope so that the pathologist can make the determination.

As discussed in greater detail below, spectral overlap may also be a problem encountered when performing multiple-color absorption analysis. However, as in the case of fluorescence, the chromatic dyes are being "activated" by specific wavelengths of light. Their response, in this case absorption, is a function of the spectral characteristics of the dye and of the incident wavelength, but is a constant for a given set of instrument settings, and the ratio of the amount of dye detected in two detection zones also remains constant. From this ratio, it can be determined what percentage of the signal produced at one detector channel comes from the dye intended to be measured at another detector channel.

Figure 2:
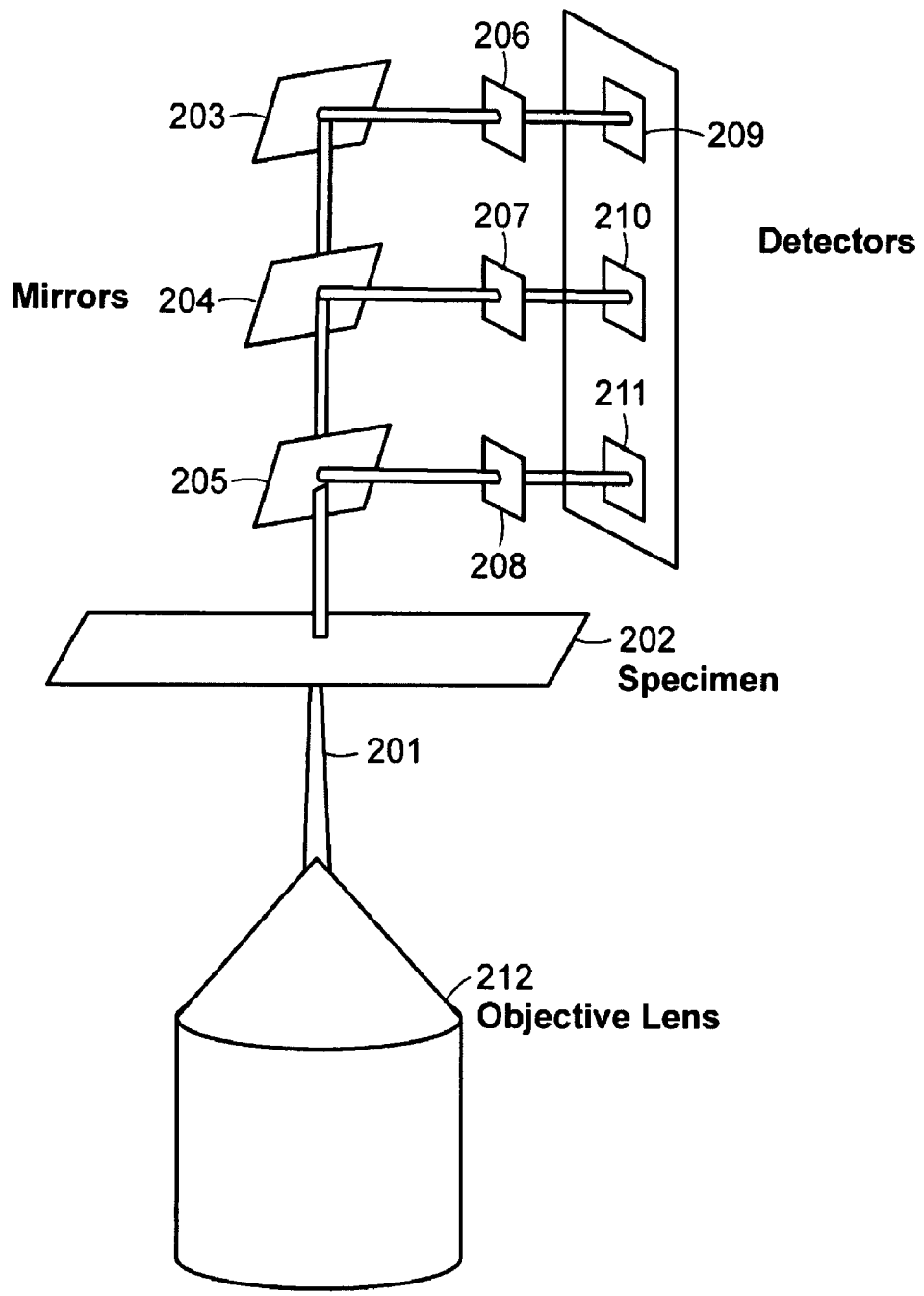
FIG. 2 is a block diagram of a multiple-color monochromatic light absorption detection system in accordance with one embodiment of the present invention, where simultaneous measurement of three colors of laser absorption is employed.

FIG. 2 is a block diagram of a multiple-color laser absorption detection system in accordance with one embodiment of the present invention. In accordance with this embodiment, simultaneous measurement of three colors of laser absorption is employed. Simultaneous measurement of three colors is realized by utilizing a lasers (or other monochromatic light sources) which are arranged such that a beams from three different colored lasers are received by a biological sample such that the beams are coaxial with one another.

Figure 4:
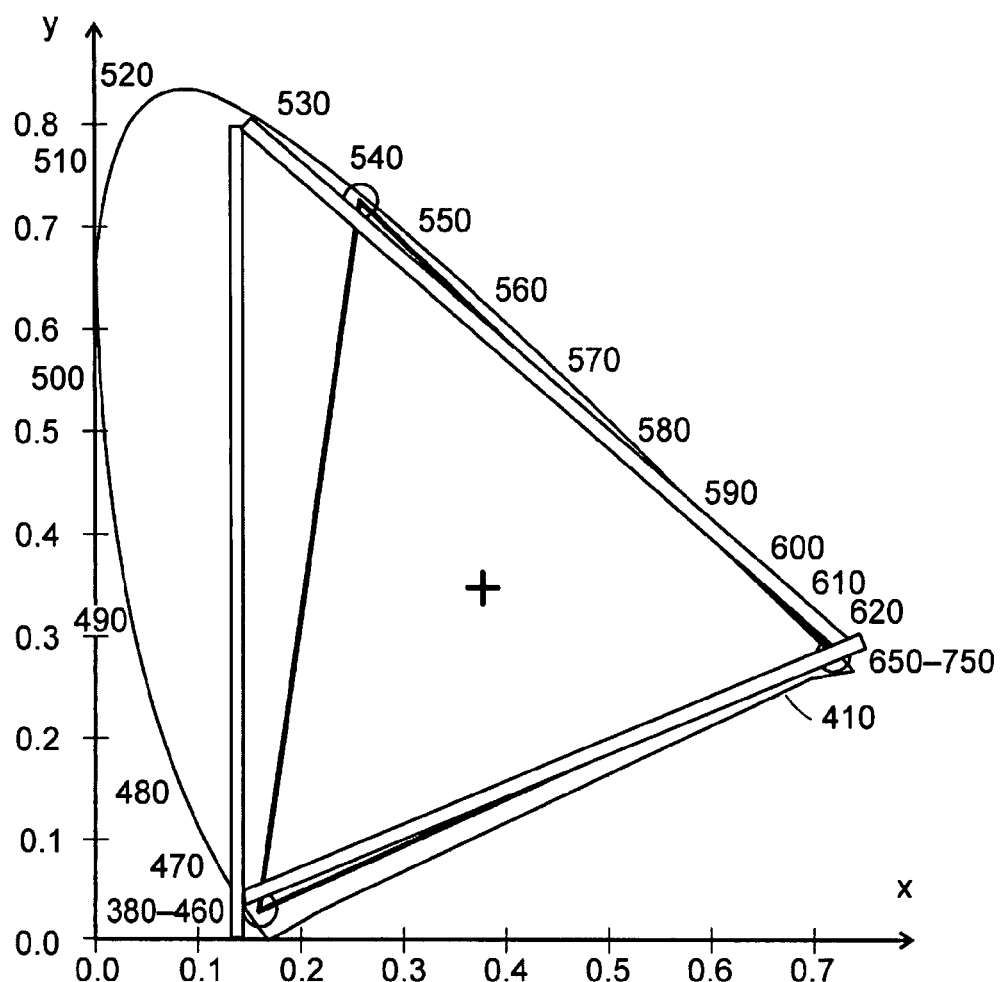
FIG. 4 is an illustration of a chromaticity diagram produced in accordance with the systems of FIGS. 2 and 3.

In accordance with the embodiment of FIG. 2, a multiple-color laser absorption detection system includes one or more laser beams 201 (in this case, three different colored beams arranged coaxially as described above) are guided by focusing optics (such as an objective lens 212) through a specimen on a microscope slide 202. The beam impinges on one or more mirrors (in this case three mirrors 203-205). Each mirror 203-205 redirects the beam to band pass filters 206-208, providing blue, green and red laser wavelengths, for example, at 440 nm, 532 nm, and 633 nm, respectively. Together, the three lasers give chromatic coverage enclosed in the triangle 401 of the chromaticity chart shown in FIG. 4. Each filtered beam is then incident upon a unique photodetector. The three detectors 209-211 allow simultaneous acquisition of spectrally distinct data. The three detectors 209-211 may each consist of a photodiode. Other detection devices, such as CCD devices, digital cameras or other apparatuses known in the art, may also be employed. In accordance with an embodiment of the invention, all three of the lasers are simultaneously impinging upon the sample. Simultaneous scanning with all three of the lasers enables a single-pass detection of the three chromatic colors, saving considerably in analysis time.

Figure 3:
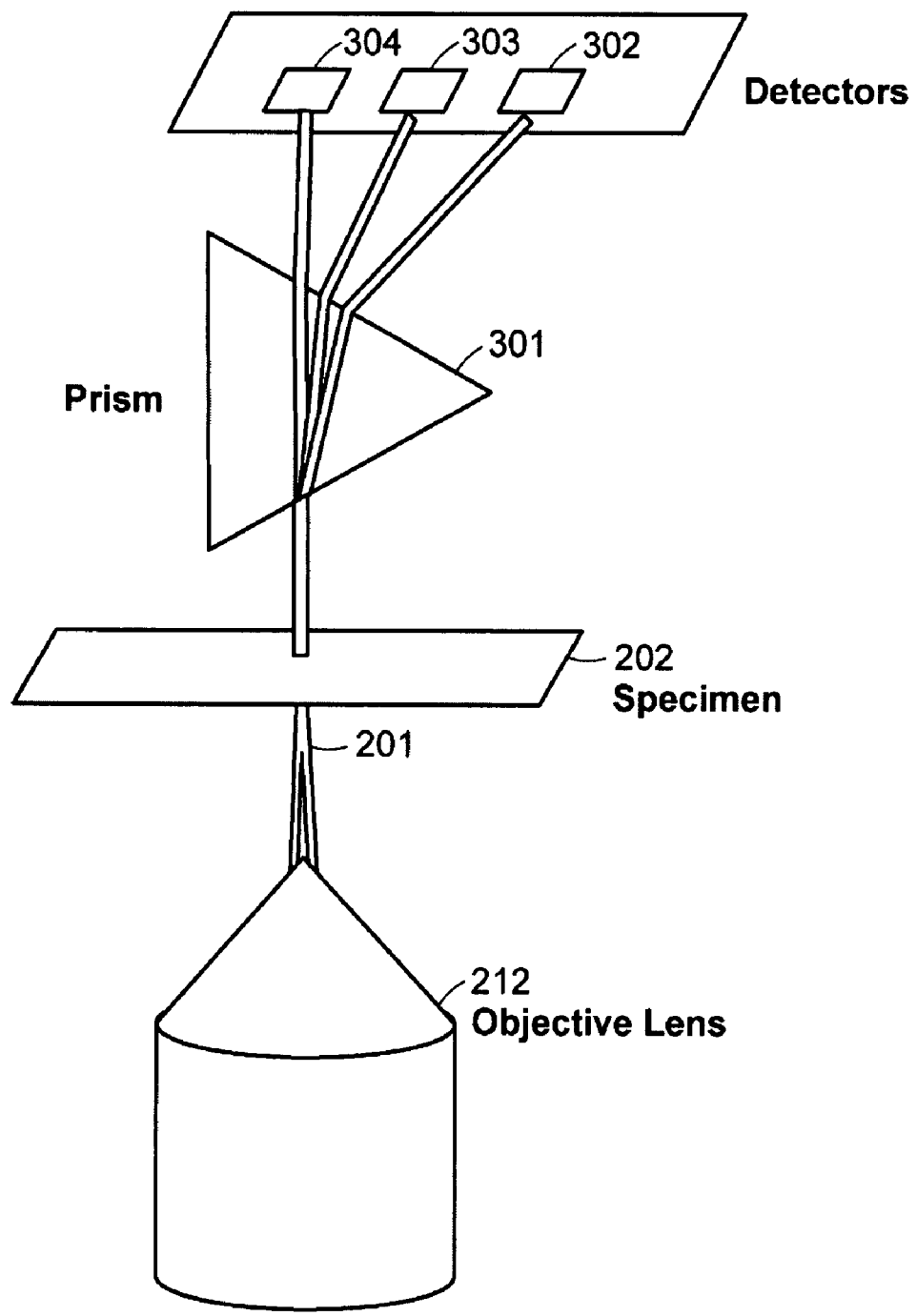
FIG. 3 is a block diagram of a multiple-color monochromatic light absorption detection system in accordance with another embodiment of the invention.
Figure 5A:
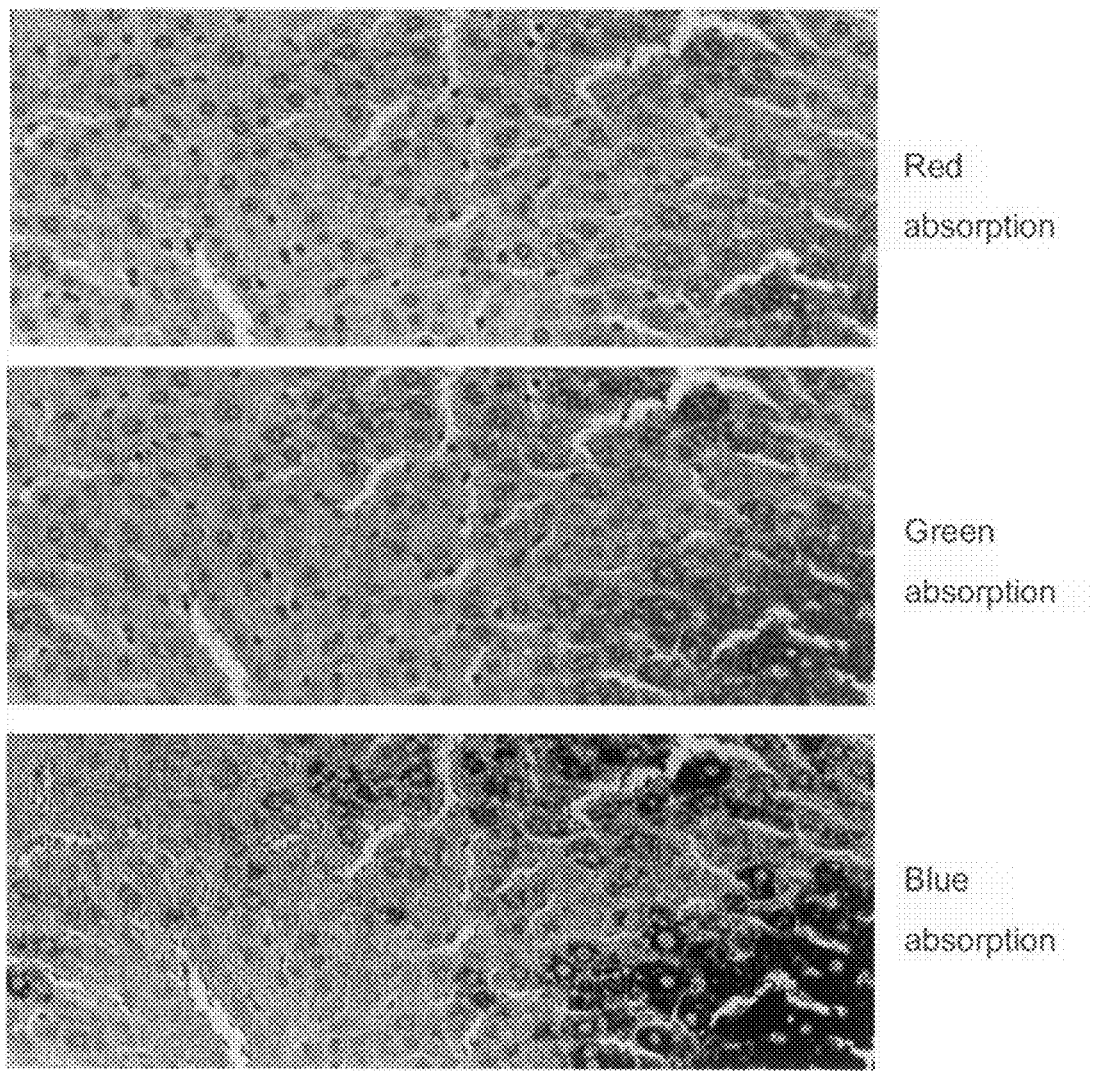
FIGS. 5A and 5B are illustrations of images produced in accordance with the multiple-color monochromatic light absorption systems of FIGS. 2 and 3, either as individual color channels or as a composite color image.
Figure 5B:
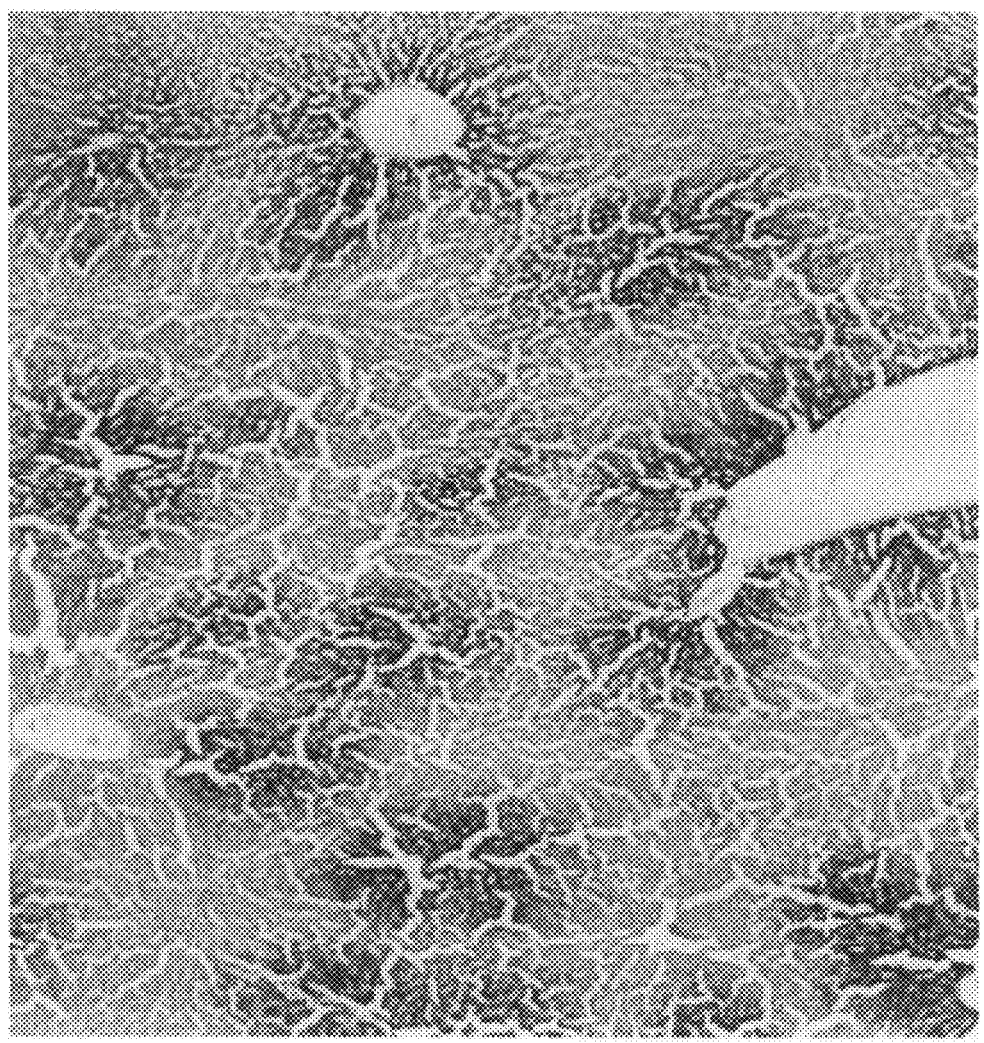

FIG. 3 is a block diagram of a multiple-color laser (or other monochromatic light) absorption detection system in accordance with another embodiment of the invention. In accordance with this embodiment, a prism 301, rather than mirrors 203-205 and band pass filters 206-208, is used to spatially separate the wavelengths of light. Detectors 302-304 as described above are then positioned to detect each of the separate wavelengths. FIG. 5A is an illustration showing images produced in accordance with the multiple-color, laser absorption systems of FIGS. 2 and 3 for the individual detectors being employed. FIG. 5B shows a composite color image produced in accordance with the multiple-color laser absorption systems of FIGS. 2 and 3.

Figure 6:
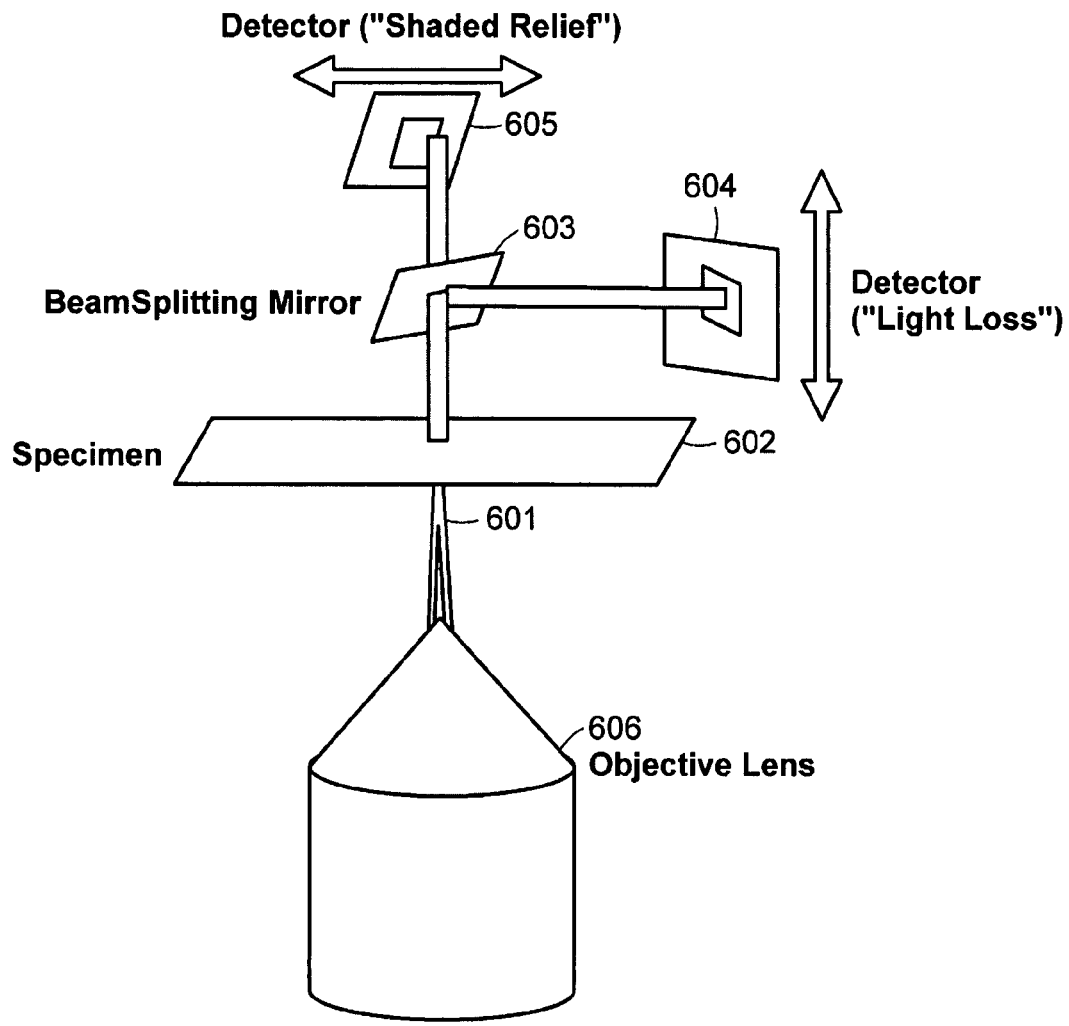
FIG. 6 is a block diagram of a two-channel monochromatic light multiple absorption mode detection system in accordance with another embodiment of the invention.
Figure 7A:
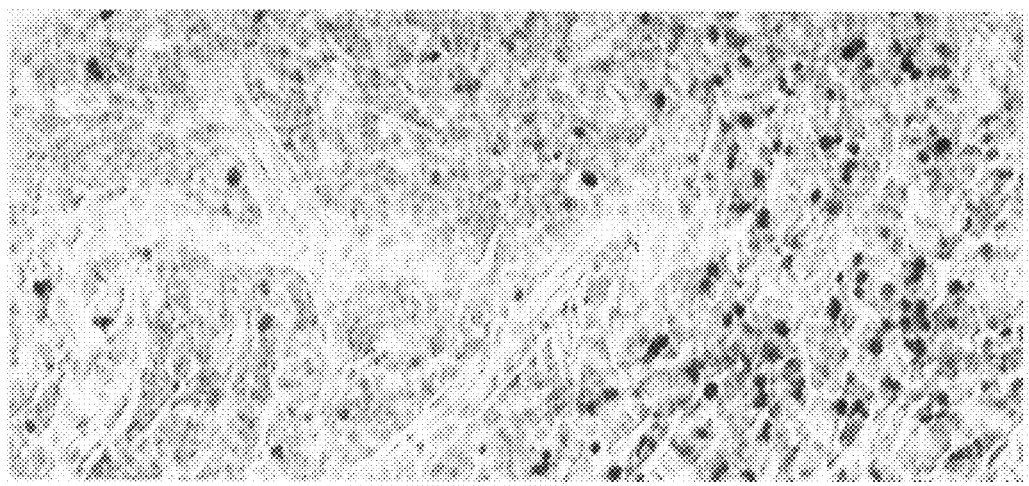
FIGS. 7A and 7B are illustrations of images produced using the detection system of in FIG. 6.
Figure 7B:
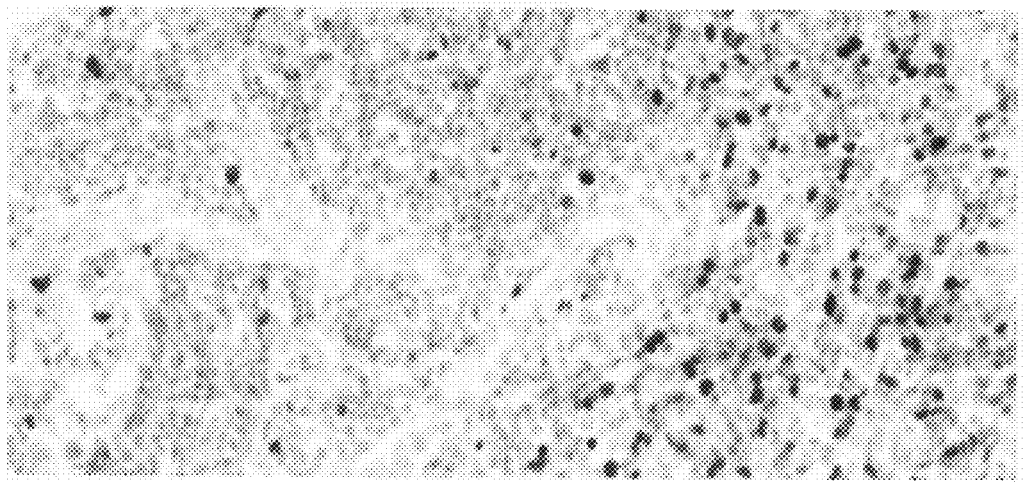

FIG. 6 is a block diagram of a two-channel monochromatic light multiple absorption mode detection system in accordance with another embodiment of the invention. As shown in FIG. 6, a laser beam 601 is guided by focusing optics (such as an objective lens 606) through a specimen on a microscope slide 602. The beam impinges on a beam-splitting mirror 603, producing transmitted and reflected beams. The two beams are directed to unique photodetectors 604 and 605. Each photodetector 604 and 605 may be manipulated independently to produce a "light loss" (combination of absorption, scatter, and refraction) signal or a "shaded relief" (forward scatter) signal respectively or some position intermediate to these two modes. In the "light loss" mode, the received signal is centered upon the photodetector, and the photodetector captures all of the laser beam directed towards the detector. In the "shaded relief" mode, the received signal impinges upon the edge of the photodetector, and the photodetector captures a portion of the laser beam directed towards the detector. The portion of the laser beam directed toward the detector may be controlled by computer software. Independent adjustment of the two photodiode modes allows for simultaneous collection of sample absorption signal (improved quantification) and the sample scattered signal (improved contrast and image quality). FIGS. 7A and 7B display images acquired using the "light loss" and "shaded relief" modes respectively.

The systems of the present invention may be computer-operated. For example, software may determine, among other things, the number of scans. The software associated with the present invention may provide the ability to do up to three successive scans with one or more lasers. This may be desirable in applications where a user may want to simultaneously quantify fluorescence markers along with the absorption. Because the interaction of the dyes with the lasers is constant, the composite signal can be compensated, adjusted or corrected. In accordance with an embodiment of the invention, the software associated with the system may compensate for spectral overlap. Spectral overlap compensation is performed in a manner similar to that used in fluorescence laser scanning cytometry images. A general formula for correction of two dyes is:

(Dye1 corrected)=(Dye 1 uncorrected)−(Dye 2 multiplied by a correction factor) wherein the correction factor is empirically determined for the combination of instrument settings.

As shown above with respect to FIGS. 7A and 7B, compensated images of the red and green inverted scatter are generated, indicating transferability of fluorescence-based techniques to the absorption method. In practical terms, this allows use of the LSC-based techniques for cellular event segmentation to evaluate and analyze the samples. To facilitate analysis using techniques developed for fluorescence-based laser scanning cytometry analysis, the images are inverted in what is called a virtual channel, so that the background levels are black, and the absorption signals are white.

Figure 8:
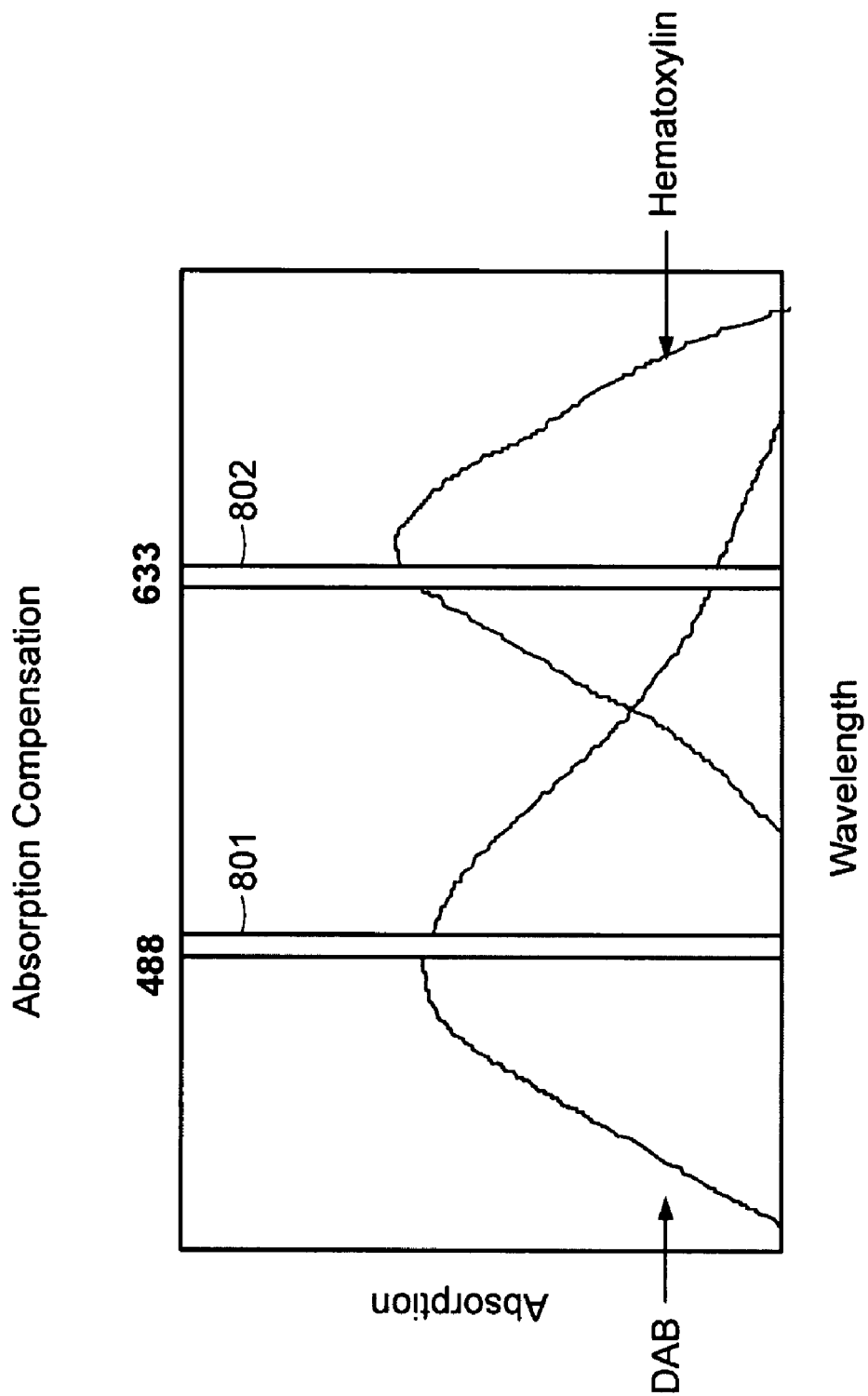
FIG. 8 is an illustration of overlapping absorption spectra for chromatic dyes employed in a multiple-color laser absorption detection system showing monochromatic light wavelengths employed in the analysis.

FIG. 8 is a graphical illustration of overlapping absorption spectra obtained in accordance with a multiple-color monochromatic light absorption detection system. In FIG. 8, two dyes, colored red and blue, have different but overlapping absorbance spectra. Both dyes absorb some amount of light from both lasers, thus the signal produced at each detector is a composite signal. The interaction of the dyes is substantially constant, thus to generate the contribution of only the red dye signal at wavelength 802, the red channel composite signal may be compensated by multiplying the signal produced by absorption of the blue dye by an empirically derived multiplication factor. This factor will correspond to the ratio of the absorbance of the blue dye at the wavelength 801 and the red dye at wavelength 802. This gives an intermediate signal, which is subtracted from the composite detected signal, removing the blue dye component from the composite signal. The remaining signal is the compensated red signal, corresponding to the red dye signal that is present at the detection wavelength 802. The same process could be applied to the blue channel composite signal to generate the contribution of only the blue dye at wavelength 801. In practice, the process is applied at the level of the laser scan images.

Figure 9A:
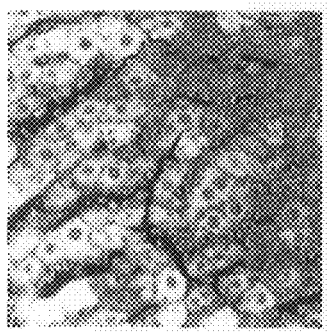
FIGS. 9A-9E are illustrations of uncompensated scan images for the three detectors employed and images showing the compensation for the spectral overlap of DAB chromogen into the green and red channels.
Figure 9B:
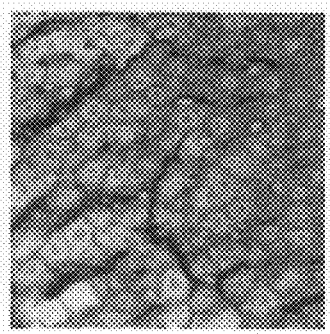
Figure 9C:
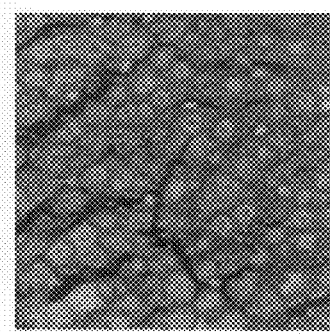
Figure 9D:
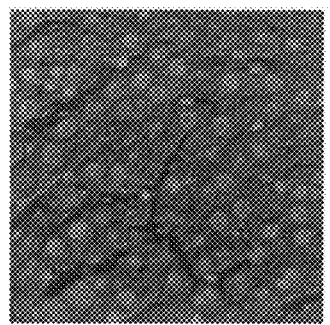
Figure 9E:
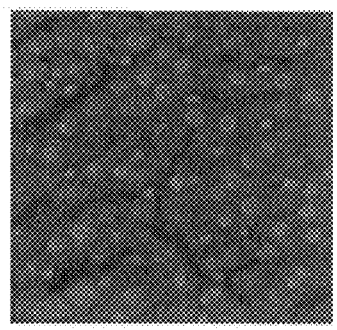
Figure 10:
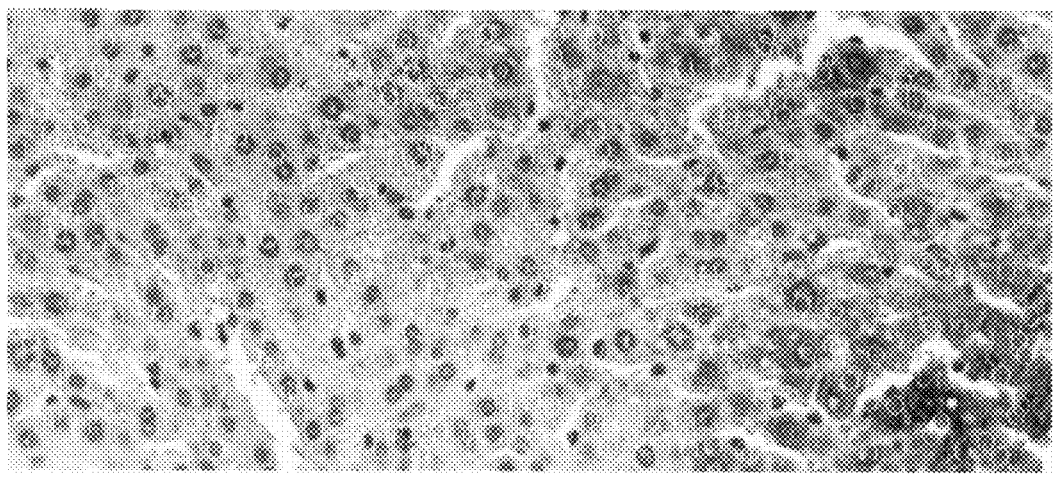
FIG. 10 is an illustration of the application of previously disclosed random sampling elements to obtain quantitative data from the corrected scan images.

FIGS. 9A-9E are illustrations of images produced before and after compensating for the spectral overlap. FIG. 9A shows the blue absorbance of a tissue section. The white areas are specific antibody staining. FIGS. 9B and 9C show the green and red absorbance, respectively, of the same scan area wherein some of the antibody signal is bleeding into the images. FIG. 9D shows the green absorbance and FIG. 9E shows the red-absorbance after the compensation is applied using the method described in relation to FIG. 6. In contrast, FIG. 10 shows the application of sampling elements according to a previously disclosed method to quantify the amount of laser absorbance for each of the photodiode detectors involved in the analysis.

Figure 12:
FIG. 12 is an illustration of an image where cell nuclei are used to segment events in a compensated image which would not have been possible the embodiments of the invention.

FIGS. 11A-11E show analytical data that was obtained without and with the compensation applied. FIG. 11A shows the blue absorbance histogram, with the specific signal colored green, red and yellow. In the green (FIG. 11B) and red (FIG. 11C) histograms, the spectral overlap is seen as the offset of the green and yellow peaks from the blue peak. In the green-compensated (FIG. 11D) and the red-compensated (FIG. 11E) histograms, all of the peaks are aligned. FIG. 12 shows a scan field of corrected red laser absorption wherein individual nuclei stained with hematoxylin are segmented without interference from overlapping dyes in the sample.

In accordance with embodiments of the invention, the absorption of N different dyes may be quantified by utilizing N monochromatic light sources of different wave lengths. Each dye may absorb a percentage of light from at least one light source. In this manner, a one-to-one correspondence may be established between each dye and a given light source. Quantification may be achieved by algebraically compensating for the overlap in absorption produced when a given dye absorbs light at more than one wavelength. Such algebraic compensation is performed by solving a system of N simultaneous equations where N is the number of dyes for which absorption is being quantified.

Compensation factors for off-color dyes (dyes not optimal for the particular laser wavelength, but providing for enough absorption to interfere with the measurement of another dye that is optimal for that laser wavelength) is determined by measuring the absorbance of the off color dye at an first wavelength (which may correspond to an optimal wavelength) and measuring the absorbance of the off color dye at a second wavelength (which may correspond to a sub-optimal wavelength). The ratio of the absorbances is used as a multiplier that is applied to the signal (or measurement) obtained at the second wavelength during sample analysis. The result obtained from the multiplication is subtracted from the measurement taken at the first wavelength to produce an accurate signal. Multiple (up to N) absorption measurements may be made simultaneously using up to N different detectors, one for each monochromatic light source.

As will be discussed in greater detail below, fluorescence emitted by a dyed sample (for example, a chromatically dyed sample) may be used to correct for the absorption signal in order to accurately quantify the amount of light loss due to the dye in the sample. Auto-fluorescence emitted by a dyed sample may also be used to correct for the absorption signal in order to accurately quantify the amount of light loss due to the dye (in accordance with the above example, a chromatic dye) in the sample. Further, intensity variations (such as systemic, optically induced variations) of the laser beams along the scan axis, as measured at the multiple-color monochromatic light absorption detectors, may be compensated for by measuring the response from the beams traveling through a blank target, and creating a per-pixel correction lookup table. Values from the per-pixel correction lookup table may be applied to raw acquired pixel values during scanning to correct for the intensity variations. The corrected data is applied to analysis and images produced by the system.

In should be noted that the above compensation process can be repeated on multiple channels in a sequential manner.

Corrections to the Images—Auto-Fluorescence Correction

Tissue auto-fluorescence interferes with quantitative chromatic dye (or other dye or absorbing material) analysis and methods and apparatuses are provided herein to correct for such interference in laser scanning-based tissue analysis. These methods and apparatuses are applicable to other sample types, including cytological and even non-biological specimens. Further, the methods may be extended to correct for the interference of chromatic (or other) dye quantification caused by fluorescent dyes that may be present within the sample. Note that although the method is illustrated herein as employing laser-based systems and a photomultiplier, it is also applicable to camera-based systems with either laser or other light sources that emit light in various ranges of the electromagnetic spectrum.

As will be explained in more detail below, the absorption of light (such as monochromatic light produced by lasers or light-emitting diodes) by chromatic dyes or other absorbing materials may be quantified.

Figure 13:
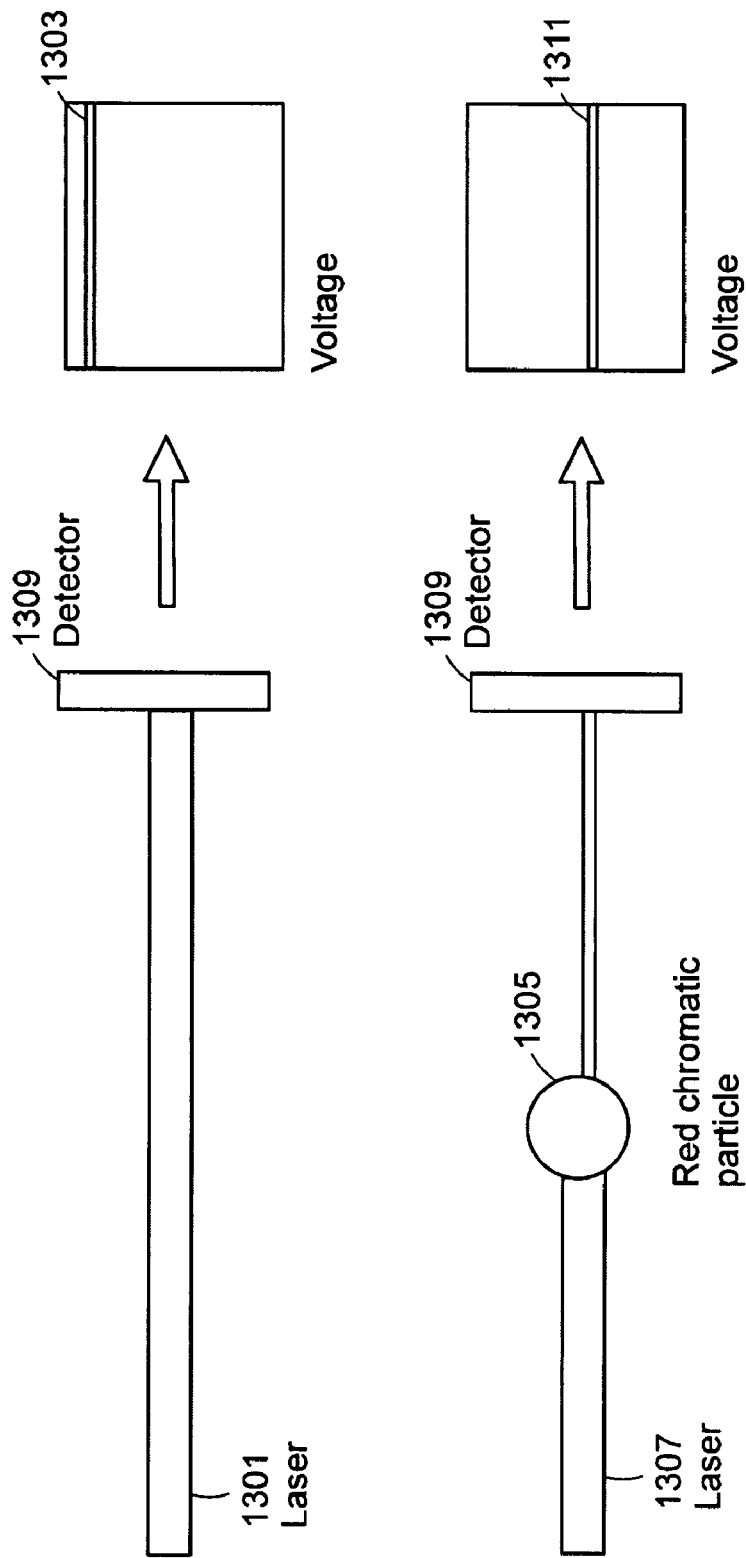
FIG. 13 is a block diagram illustrating laser light loss associated with a chromatic particle.

FIG. 13 is a block diagram illustrating laser light loss associated with a chromatic particle. The amount of chromatic dye expression in tissue sections or other samples can be quantified by measuring the light loss of an interrogating laser (or other light) beam. The measurement systems are typically calibrated by establishing a reference signal for the laser beam 1301 after it passes through a carrier platform with no sample present. The reference signal is set to a high level as shown at 1303. When a chromatically labeled entity 1305 is in the path of a laser beam 1307, laser light is absorbed, and there is a reduction in the amount of laser light that impinges on detector 1309 (typically a photodiode). The signal change, shown at 1311, is referred to as light loss and is used as a metric to quantify the amount of chromatic label in the laser's path.

Figure 14:
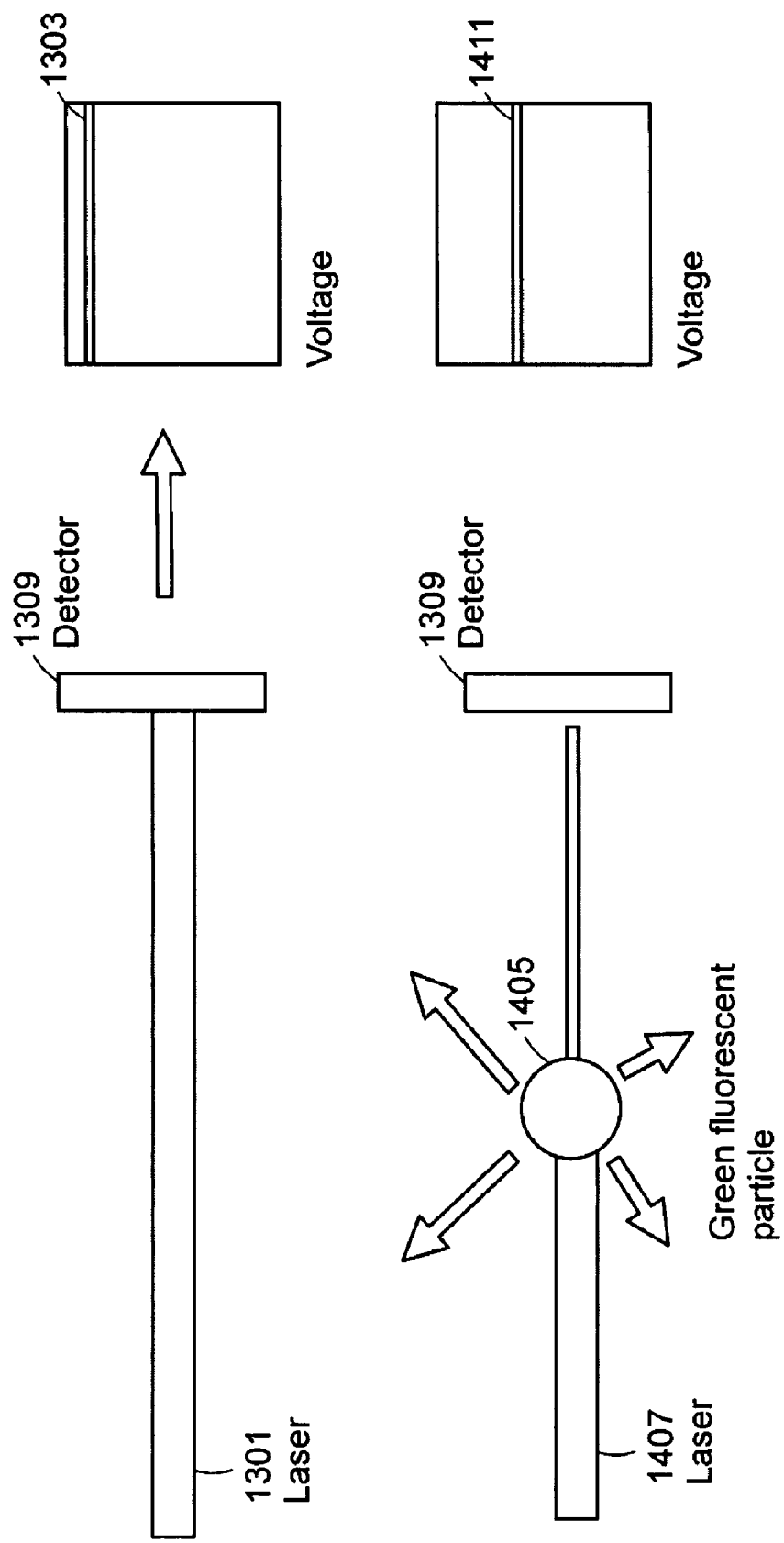
FIG. 14 is a block diagram illustrating laser light loss associated with a fluorescent particle.

FIG. 14 is a block diagram illustrating laser light loss associated with a fluorescent particle. Here, laser light loss is produced by a fluorescent or auto-fluorescent particle 1405 in the path of a laser beam 1407. The amount of laser light that impinges on the detector 1309 is reduced and this reduction produces a voltage change from the level shown at 1303 to the level shown at 1411.

Figure 15:
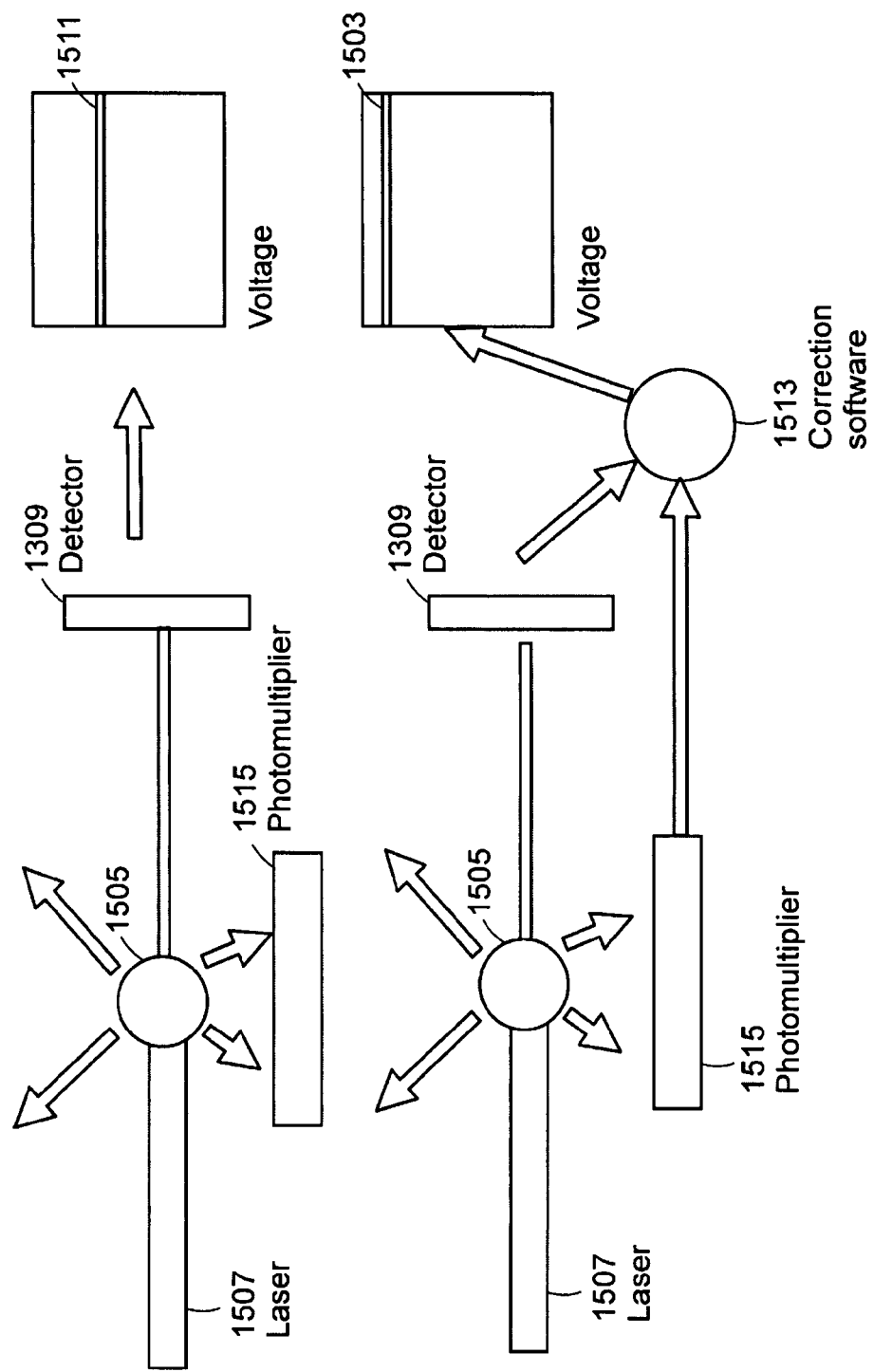
FIG. 15 is a block diagram illustrating how measured green fluorescence may be used to restore the baseline voltage level in accordance with an embodiment of the invention.

FIG. 15 is a block diagram illustrating how measured green fluorescence may be used to restore the baseline voltage level in accordance with an embodiment of the invention. In accordance with embodiments of the present invention, the amount of green fluorescence emitted by a particle 1505 in the pathway of the laser beam 1507 is measured using a photomultiplier tube 1515. The amount of fluorescence emitted is an indicator of the amount of light that was lost from the laser beam 1507 due to conversion to fluorescence. Computer software or analog electronic circuitry 1513 (which may contain standard components such as operational amplifiers to modify the voltage signals) are used to apply a correction factor to the photodiode detector to restore the baseline 1511 to the baseline level 1503 in order to measure chromatic dye-based light loss.

Auto-Fluorescence Correction—Example Procedure

The analysis technique that follows is based on the following reasoning: 1) green auto-fluorescence is detected at the same time that blue light-loss signal is obtained; 2) for green auto-fluorescence to occur, there must have been conversion of the exciting 488 nm laser light into green light; 3) the laser light that is converted to green fluorescence is lost to the blue scatter detector; and 4) this gives an artificially high measurement of specific blue-laser absorption. To correct for this artifact, the green fluorescence signal (or an adjusted signal based on it) may be subtracted from the inverted blue light loss signal. Subtracting the green fluorescence signal from the inverted signal is mathematically equivalent to adding it to the non-inverted signal. Thus, in effect, a correction factor may be added to the inverted blue light loss signal to compensate for the amount of laser light that was lost to fluorescence.

To illustrate the method, tissue sections stained with antibodies to a specific antigen and developed with the chromatic dye diaminobenzidine (DAB) were analyzed on a laser scanning cytometer. The slides were segregated into groups that either had no staining (exhibiting only background levels of staining), or varying amounts of specific staining. Quantification of the amount of DAB staining was the goal of this particular experiment.

Figure 16:
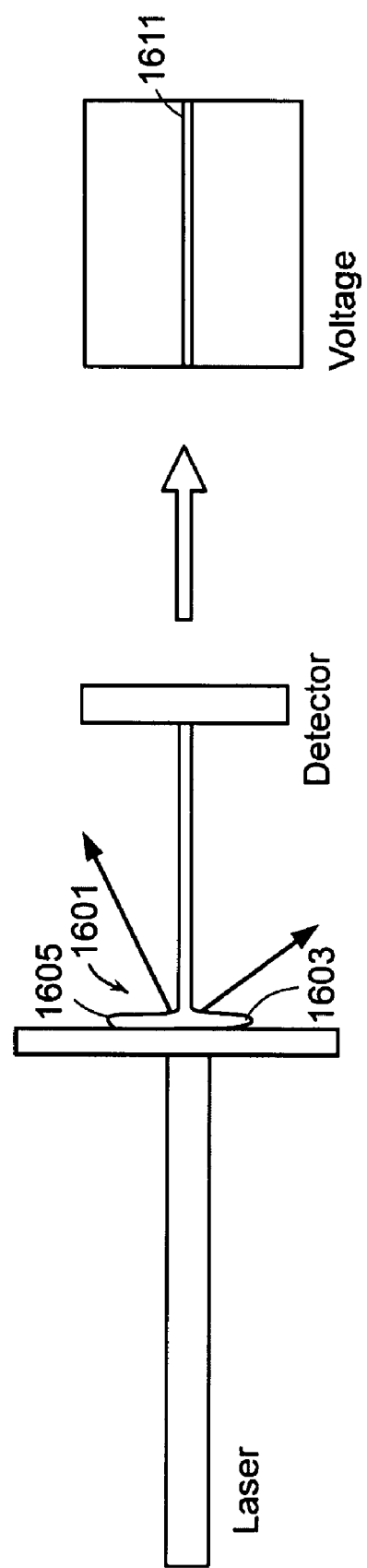
FIG. 16 is a block diagram illustrating a tissue section with both fluorescent and chromatic components that may contribute to light loss.

As shown in FIG. 16, a tissue section (or other cellular sample) 1601 may include both fluorescent and chromatic components (1603 and 1605 respectively) which contribute to light loss. Thus, when analyzed by laser scanning cytometry, these tissue sections exhibited both light loss and green fluorescence. The fluorescence was caused by auto-fluorescence of the tissue. The light loss indicated by voltage 1611 can be caused by either chromatic or fluorescent entities within the tissue. The light loss caused by the auto-fluorescent components was not of interest in this example as it interferes with the assay sensitivity.

Figure 17:
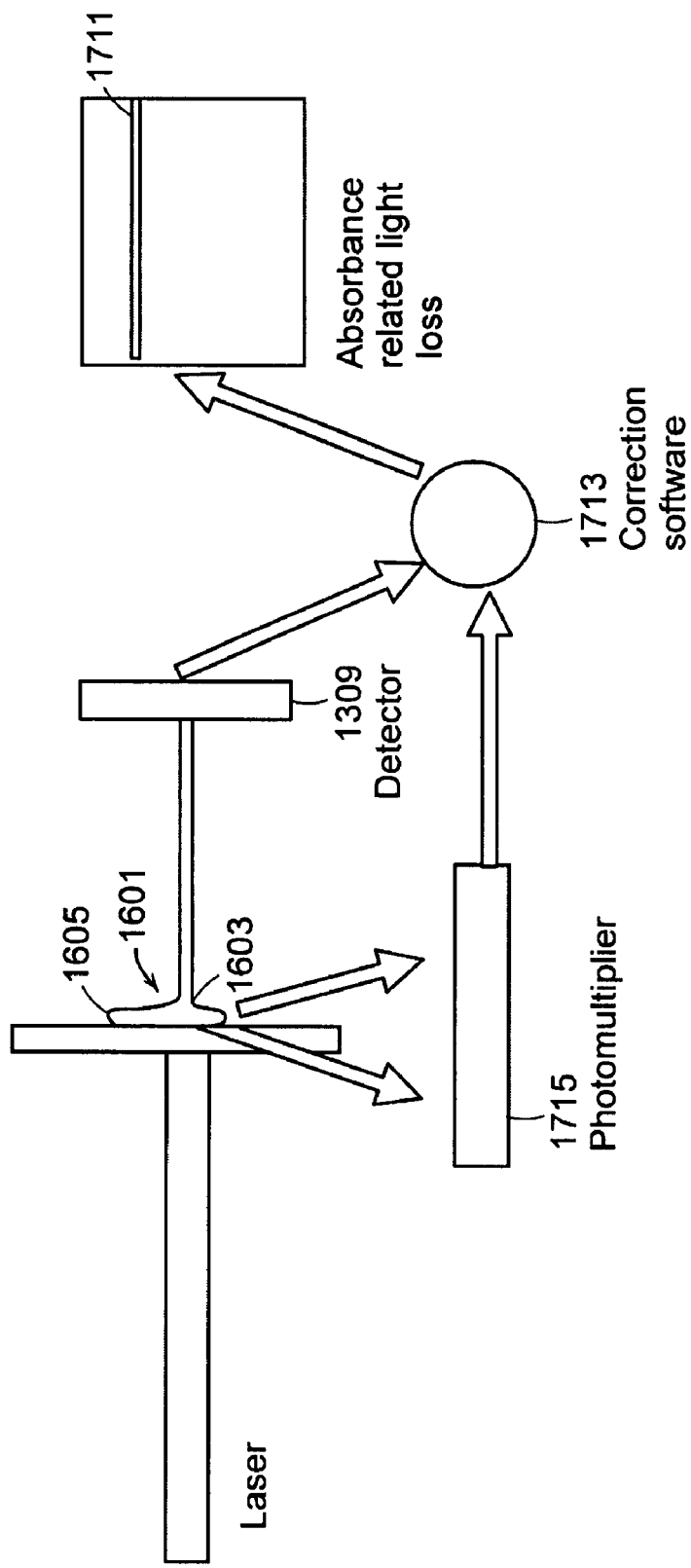
FIG. 17 is a block diagram illustrating how measurement of the green fluorescence may be used to correct the light loss signal of FIG. 16 to be specific for chromatic light loss in accordance with another embodiment of the invention.

As shown in FIG. 17, a photomultiplier tube 1715 was introduced into the system of FIG. 16 to measure the amount of green fluorescence. The photomultiplier tube 1715 was used as an input for the computer correction algorithms 1713, and the effect of the auto-fluorescence on the light loss signal was effectively eliminated from the analysis system such that the signal 1711 indicates light loss due to absorbance of light by the stained sample.

Figure 18:
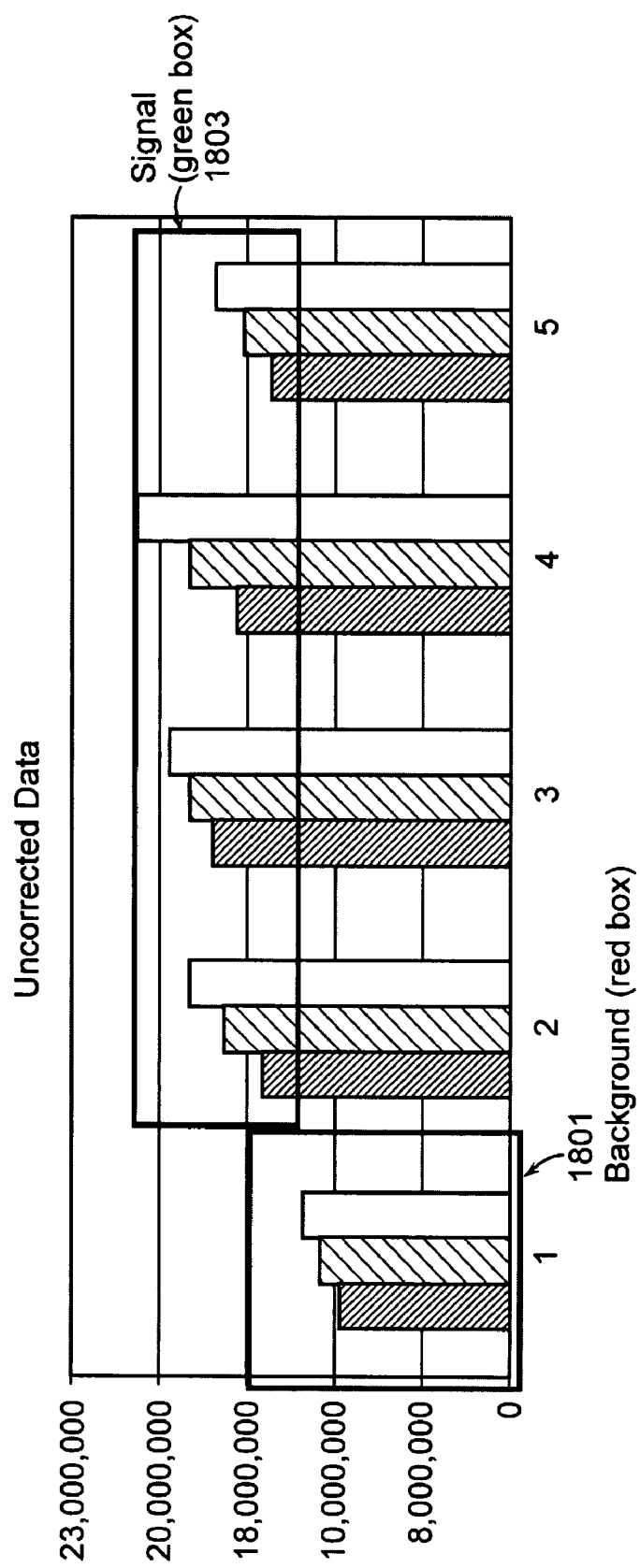
FIG. 18 is an illustration showing the signal-to-noise ratios in a data set representing an uncorrected light loss signal.
Figure 19:
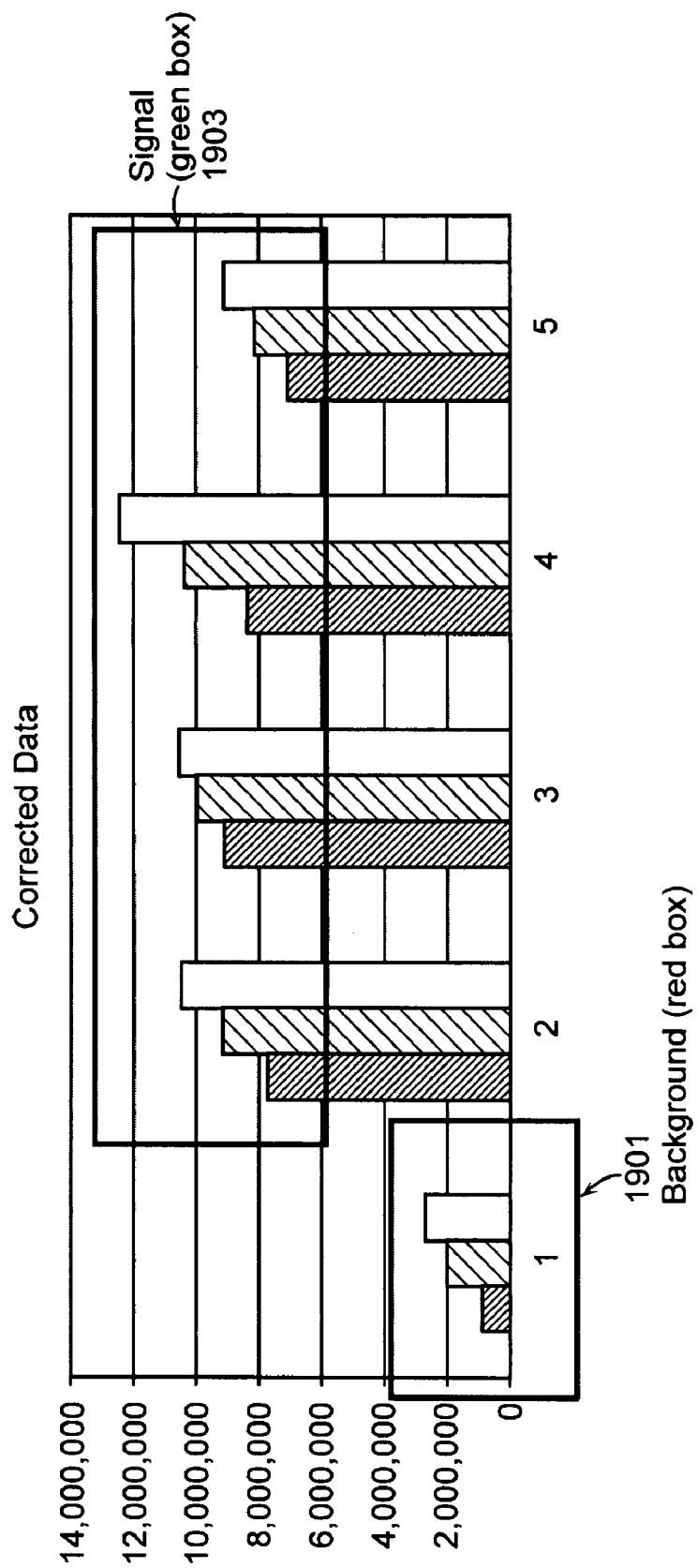
FIG. 19 is an illustration showing the increased signal-to-noise ratios in a data set representing a light loss signal corrected in accordance with an embodiment of the invention.

The efficacy of the correction algorithm is shown in the graphs of experimental data shown in FIGS. 18 and 19. The analysis results from five groups of slides are shown as uncorrected data in FIG. 18 and corrected data in FIG. 19. A red box 1801 and 1901 has been drawn around the background-level control group and a green box 1803 and 1903 has been drawn around the groups expressing specific chromatic dye staining. As can be seen from the graphs of FIGS. 18 and 19, the ratio of the specific signal to background staining is greatly increased in the corrected group.

Figure 20:
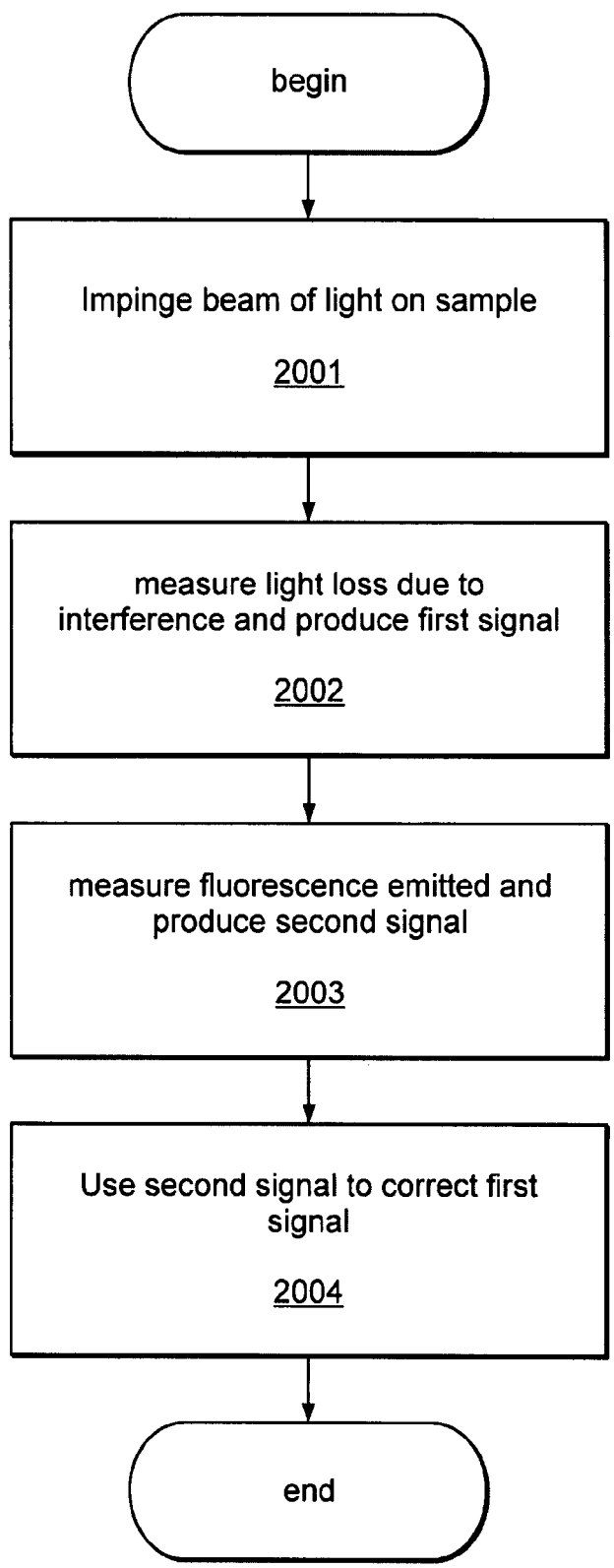
FIG. 20 is a flow chart illustrating a method for quantifying the light absorption in a biological sample.

FIG. 20 is a flow diagram illustrating a method for quantifying the light absorption in a biological sample. In accordance with this embodiment, a beam of light is impinged 2001 on the sample. An amount of light loss due to interference of the beam by the sample is measured and a first signal is produced 2002. An amount of fluorescence emitted by the sample is also measured and a second signal is produced 2003. The second signal is used 2004 to correct the first signal in order to quantify the amount of light loss due to a chromatic dye in the sample.

The example shown above corrects for auto-fluorescence, but similar strategies can be used to correct for the effects of fluorescent dyes on light-loss signals. Additionally, the method described above may be applied to samples other than tissue sections. Further, the method may also be applied to camera-based systems.

Corrections to the Input Signals—Per Pixel Correction

Due to the nature of the scanning optics, the intensity of the laser beams varies as it scans across the specimen in a Y (or vertical) direction. Corrections for this variation for fluorescence measurements include empirically measuring the intensity of calibration particles at a plurality of positions that cover the entire scan field. In accordance with fluorescence-based analysis, the mean of the fluorescence intensity of the particles is calculated for each possible Y position and a correction factor is calculated for each Y position. These calculated values are and stored in the look-up table. In subsequent image acquisition, the detector values may be multiplied by the correction factor to obtain the background corrected data (see, for example, U.S. Pat. No. 5,885,840).

Figure 21:
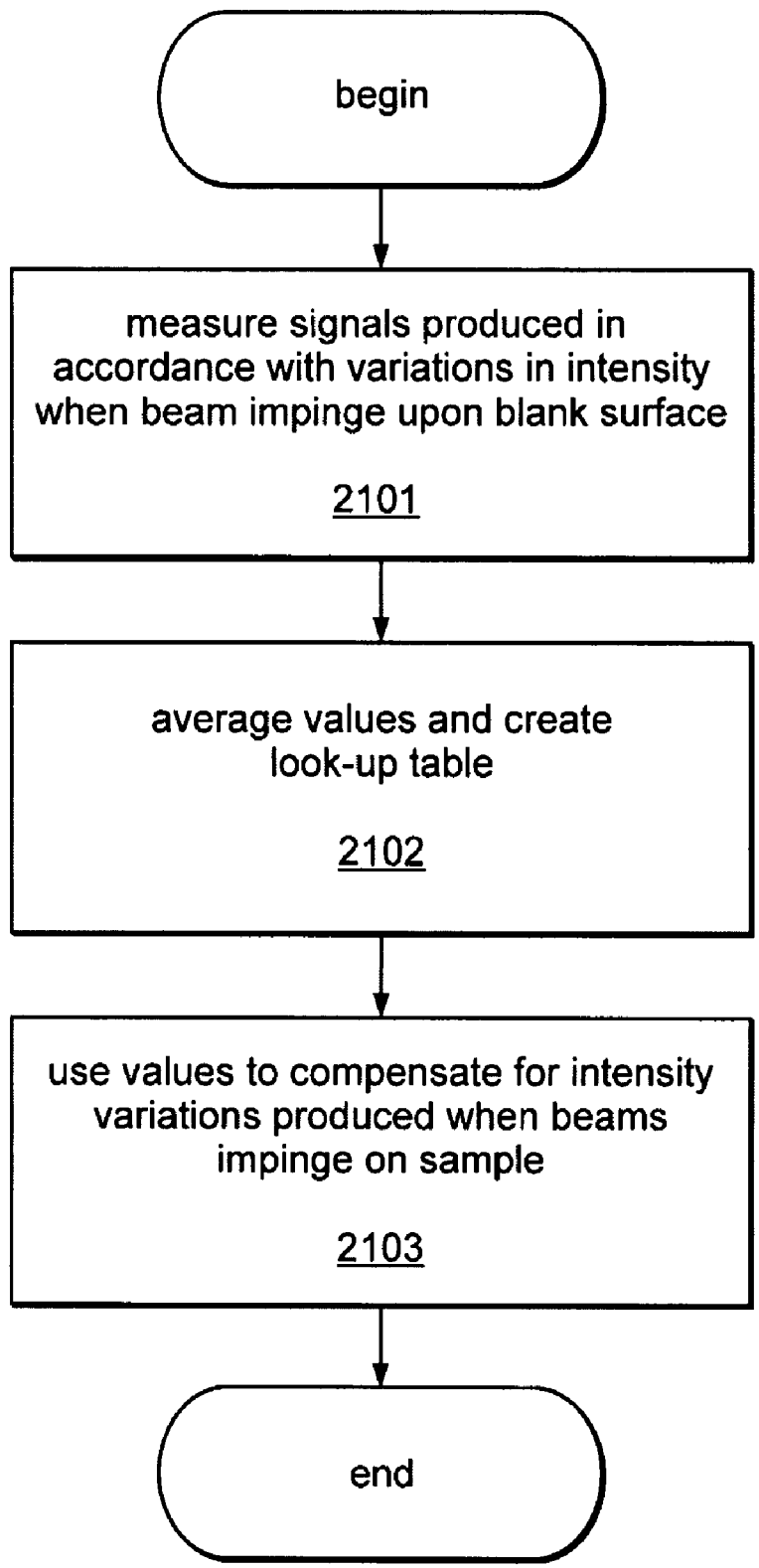
FIG. 21 is a flow chart illustrating a method for correcting input signals associated with light absorption in a biological sample.

For light scatter absorption measurements, the same principle is applied, but instead of using calibration particles, a blank microscope slide is used. The photodetectors are set to give a signal in the working range of the instrument, usually near the upper limits of absorbance detection, and laser scans are obtained. FIG. 21 is a flow chart illustrating a method for correcting input signals associated with light absorption in a biological sample. In accordance with this embodiment, signals produced in accordance with the variations of intensity are measured 2101 when the beams impinge upon a blank surface. Values for each pixel across the scan line are averaged across the group of laser scans and a per-pixel correction lookup table is produced 2102 and values associated with the signals produced when the beams impinge upon the blank surface are used 2103 to compensate for intensity variations produced when the beams impinge upon the sample. In subsequent image acquisition, the detector values are multiplied by the correction factor to obtain the background corrected data. The corrected data is available for viewing and analysis in image displays with improved accuracy of the quantitative data. FIGS. 22A and 22B are illustrations of light absorption images produced before and after per-pixel correction is applied, respectively.

It should be understood that various changes and modifications to the preferred embodiments described above will also be apparent to those skilled in the art. Modifications can be made without departing from the spirit and scope of the invention and without diminishing its attendant advantages.

What is claimed is:

1. A laser scanning cytometer including an absorption detection system, the absorption detection system comprising:
    a plurality of monochromatic light sources arranged for directing light at a biological sample so that the biological sample in the laser scanning cytometer is scanned by the light;
    a separator configured to separate the light that has passed through the biological sample into a plurality of beams respectively corresponding to wavelengths of light; and
    a plurality of detectors, each of the detectors corresponding to a respective wavelength of light to measure absorption of light in a biological sample at the respective wavelength of light.

2. A laser scanning cytometer according to claim 1, wherein the biological sample contains a dye.

3. A laser scanning cytometer according to claim 1, wherein at least one monochromatic light source is a laser.

4. A laser scanning cytometer according to claim 1, wherein a beam of light from each of the plurality of monochromatic light sources is received by the sample such that the beams are coaxial.

5. A laser scanning cytometer according to claim 1, wherein the separator includes a beam-splitting mirror for receiving light from the monochromatic light sources.

6. A laser scanning cytometer according to claim 5, wherein the separator includes a band-pass filter for receiving light from the beam-splitting mirror.

7. A laser scanning cytometer according to claim 1, wherein the separator includes a prism.

8. A laser scanning cytometer according to claim 1, wherein at least one detector includes a photodiode.

9. A laser scanning cytometer according to claim 1, wherein at least one detector includes a photomultiplier tube.

10. A laser scanning cytometer according to claim 1, wherein a signal from a first one of the detectors is used to modify the signal from a second one of the detectors to obtain a corrected value of absorbance of light in the sample at the respective wavelength corresponding to the second one of the detectors.

11. A laser scanning cytometer according to claim 2, wherein one of the wavelengths of the monochromatic light sources substantially corresponds to a spectral peak of absorption of the dye.

12. A method for detecting light absorption in a laser scanning cytometer, the method comprising:
    scanning a biological sample on a carrier in a laser scanning cytometer with light from a plurality of monochromatic beams of light;
    separating the light from the plurality of monochromatic beams of light that has passed through the biological sample on the carrier into spatially distinct transmitted monochromatic beams; and
    detecting the light in the spatially distinct transmitted monochromatic beams with beam detectors each corresponding to one of the spatially distinct transmitted monochromatic beams, the beam detectors generating registered signals to measure absorption of the light in the biological sample.

13. A method according to claim 12, where scanning the biological sample on the carrier with light from the monochromatic beams includes scanning the biological sample on the carrier with a laser beam.

14. A method according to claim 12, wherein scanning the biological sample on the carrier with light from the monochromatic beams includes scanning the biological sample on the carrier with light from a plurality of coaxial beams.

15. A method according to claim 12, wherein separating the light that has passed through the sample on the carrier includes receiving the light at a mirror.

16. A method according to claim 15, further comprising:
    receiving the light reflected from the mirror at a plurality of band-pass filters.

17. A method according to claim 12, wherein separating the light that has passed through the sample on the carrier includes receiving the light at a prism.

18. A method according to claim 12, wherein detecting the light with the beam detectors includes detecting the light with at least one photodiode.

19. A method according to claim 12, wherein detecting the light with the beam detectors includes detecting the light with at least one photomultiplier tube.

20. A method according to claim 12, wherein scanning a biological sample on a carrier with light from the plurality of monochromatic beams of light includes scanning a biological sample on a carrier with N monochromatic beams of light and wherein detecting light with each of the beam detectors to measure absorption of light in the sample includes detecting light in each of the spatially distinct transmitted monochromatic beams at each of the beam detectors to measure the absorption of N dyes in the sample, the method further comprising:
    establishing a one-to-one correspondence between each of the N dyes and each of the plurality monochromatic beams of light.

21. A method according to claim 20, wherein establishing a one-to-one correspondence includes algebraically compensating for overlaps in absorption spectra of the N dyes.

22. A method according to claim 21, wherein algebraically compensating for the overlaps in absorption spectra includes solving a system of N simultaneous equations.

23. A method according to claim 21, wherein at least one of the N dyes comprises an off-color dye and wherein algebraically compensating for the overlaps in absorption spectra due to any of the N dyes absorbing light of more than one beam from the plurality of monochromatic beams includes:
    reducing values of the registered signals based on values of absorbance for each of N dyes, the values of absorbance being empirically determined with each of the plurality of monochromatic beams.

24. A method according to claim 12, wherein the sample contains a dye and detecting light in the plurality of spatially distinct monochromatic beams to measure absorption in the sample containing a dye includes detecting fluorescence emitted by the sample containing the dye and further comprises:

using a signal produced by the fluorescence to quantify the absorption in the sample containing the dye.

25. A method according to claim 12, wherein the sample contains a dye and detecting light in the plurality of spatially distinct monochromatic beams to identify absorption in the sample containing the dye includes detecting auto-fluorescence emitted by the sample containing the dye and further comprises:

using a signal produced by the auto-fluorescence to quantify the absorption in the sample containing the dye.

26. A method according to claim 12, further comprising:

measuring signals produced in accordance with variations of intensity of the plurality of monochromatic beams of light when the beams traverse an empty carrier;

creating a per-pixel correction lookup table containing values associated with the measured signals; and using values associated with the signals produced in accordance with variations of intensity of the plurality of monochromatic beams when the beams traverse the empty carrier for numerically offsetting measuring signals produced in accordance with variations of intensity when the beams traverse the sample on the carrier.

27. A method for quantifying the light absorption in a sample with a use of a system comprising a source of light, a first detector and a second detector, the method comprising:

impinging a beam of light on the sample;

measuring an amount of light loss due to interference of the beam by the sample with the first detector and producing a first signal;

measuring an amount of fluorescence emitted by the sample with the second detector and producing a second signal; and using the second signal to correct the first signal in order to quantify the amount of light loss due to a dye in the sample.

28. A method according to claim 27, wherein measuring the amount of fluorescence emitted by the sample includes measuring the amount of auto-fluorescence emitted by the sample.

29. A method according to claim 27, wherein measuring the amount of fluorescence emitted by the sample includes measuring the amount of green fluorescence emitted by the sample.

30. A method according to claim 27, wherein impinging a beam of light on the sample includes impinging at least one laser beam of light on the sample.

31. An absorption detection system comprising:

a plurality of monochromatic light sources arranged for directing light at a biological sample so that the biological sample is scanned by the light;

a separator configured to separate the light that has passed through the biological sample into a plurality of beams respectively corresponding to wavelengths of light; and a plurality of detectors, each of the detectors corresponding to a respective wavelength of light to measure absorption of light in a biological sample at the respective wavelength of light, wherein a signal from a first one of the detectors is used to modify the signal from a second one of the detectors to obtain a corrected value of absorbance of light in the sample at the respective wavelength corresponding to the second one of the detectors.

32. A method for detecting light absorption, the method comprising:

scanning a biological sample on a carrier with light from a plurality of monochromatic beams of light;

separating the light from the plurality of monochromatic beams of light that has passed through the biological sample on the carrier into spatially distinct transmitted monochromatic beams; and detecting the light in the spatially distinct transmitted monochromatic beams with beam detectors each corresponding to one of the spatially distinct transmitted monochromatic beams, the beam detectors generating registered signals to measure absorption of the light in the biological sample;

measuring signals produced in accordance with variations of intensity of the plurality of monochromatic beams of light when the beams traverse an empty carrier;

creating a per-pixel correction lookup table containing values associated with the measured signals; and using values associated with the signals produced in accordance with variations of intensity of the plurality of monochromatic beams when the beams traverse the empty carrier for numerically offsetting measuring signals produced in accordance with variations of intensity when the beams traverse the sample on the carrier.

* * * * *